US012369778B2

(12) United States Patent
Prater

(10) Patent No.: US 12,369,778 B2
(45) Date of Patent: Jul. 29, 2025

(54) METHOD AND APPARATUS FOR FIBER OPTIC PHOTOTHERMAL IMAGING AND SPECTROSCOPY

(71) Applicant: Photothermal Spectroscopy Corp., Santa Barbara, CA (US)

(72) Inventor: Craig Prater, Santa Barbara, CA (US)

(73) Assignee: Photothermal Spectroscopy Corp., Santa Barbara, CA (US)

( * ) Notice: Subject to any disclaimer, the term of this patent is extended or adjusted under 35 U.S.C. 154(b) by 209 days.

(21) Appl. No.: 18/003,131

(22) PCT Filed: Jun. 25, 2021

(86) PCT No.: PCT/US2021/039053
§ 371 (c)(1),
(2) Date: Dec. 22, 2022

(87) PCT Pub. No.: WO2021/263083
PCT Pub. Date: Dec. 30, 2021

(65) Prior Publication Data
US 2023/0251190 A1    Aug. 10, 2023

Related U.S. Application Data

(60) Provisional application No. 63/044,921, filed on Jun. 26, 2020.

(51) Int. Cl.
*A61B 1/00* (2006.01)
*G01J 3/42* (2006.01)
(Continued)

(52) U.S. Cl.
CPC ............ *A61B 1/00167* (2013.01); *G01J 3/42* (2013.01); *G01N 21/359* (2013.01); *G01N 2021/3595* (2013.01)

(58) Field of Classification Search
CPC . A61B 1/00167; A61B 5/0075; A61B 5/0086; G01J 3/42; G01J 2001/4242;
(Continued)

(56) References Cited

U.S. PATENT DOCUMENTS 2,940,355 A     6/1960   Cary
5,694,215 A  *  12/1997  Carver ................... G01N 30/74
                                                    356/300

(Continued)

FOREIGN PATENT DOCUMENTS

WO         2008048613 A2     4/2008

OTHER PUBLICATIONS

Yao, Chenyu, et al. "MIR-Pump NIR-Probe Fiber-Optic Photothermal Spectroscopy With Background-Free First Harmonic Detection", IEEE Sensors Journal vol. 20(Iss. 21), IEEE (Jun. 11, 2020). Jun. 11, 2020. p. 12709-12715. (Year: 2020).*

(Continued)

*Primary Examiner* — Courtney D Thomas
(74) *Attorney, Agent, or Firm* — MERCHANT & GOULD P.C.

(57) ABSTRACT

Improvements in spectroscopy are disclosed herein that rely on the interaction of both an infrared beam and a probe beam with a sample. These beams are used in a pump-probe arrangement, with a fiber optic probe collecting the beams of infrared and probe radiation from the infrared source and delivering it to the sample. At least a portion of the beam of infrared radiation and the beam of probe radiation overlap one another on the sample. The fiber also collects probe radiation that has interacted with the sample. A detector can use this collected signal to indicate an intensity of the collected probe radiation, and an analyzer can generate a signal indicative of infrared absorption of the sample adjacent the fiber.

37 Claims, 13 Drawing Sheets

(51) Int. Cl.
*G01N 21/359* (2014.01)
*G01N 21/35* (2014.01)

(58) Field of Classification Search
CPC ........... G01J 2003/102; G01J 2003/104; G01J 2003/423; G01J 2003/4334; G01J 3/0208; G01J 3/0218; G01J 3/0248; G01J 3/0278; G01J 3/10; G01J 3/108; G01J 3/427; G01J 3/44; G01J 3/433; G01N 21/359; G01N 2021/3595; G01N 21/171; G01N 21/474; G01N 21/645; G01N 21/65; G01N 2021/4709; G01N 2021/4742; G01N 2021/6484; G01N 2201/0221; G01N 21/3563; A61K 45/06; A61P 25/28
See application file for complete search history.

(56) References Cited

U.S. PATENT DOCUMENTS

| | | | |
|---|---|---|---|
| 7,630,081 | B2 | 12/2009 | Ressler |
| 9,091,594 | B2 | 7/2015 | Furstenberg |
| 2005/0027164 | A1 | 2/2005 | Barbato |
| 2005/0062971 | A1 | 3/2005 | Salnik |
| 2017/0146455 | A1 | 5/2017 | Maentele |
| 2017/0299508 | A1 | 10/2017 | Jin |
| 2019/0120753 | A1 | 4/2019 | Prater |
| 2019/0290111 | A1* | 9/2019 | Shademan ........... H04N 23/957 |
| 2019/0368939 | A1 | 12/2019 | Vakhshoori |
| 2020/0025677 | A1* | 1/2020 | Prater .................. G01N 21/65 |
| 2020/0073103 | A1 | 3/2020 | Wang |
| 2020/0085285 | A1 | 3/2020 | Yamada |
| 2020/0041410 | A1 | 4/2020 | Ashrafi |

OTHER PUBLICATIONS

Karl-Heinz Walker and Heinz Sontag "Fiber optic based chemical sensor system for in-situ process measurements using the photothermal effect", Proc. SPIE 1510, Chemical and Medical Sensors, (Sep. 1, 1991); (Year: 1991).*
International Search Report and Written Opinion for PCT/US20/039053, mailed Oct. 4, 2021, 3 pages.
Mark A. Mackanos, et al., "Fiber-optic probes enable cancer detection with FTIR spectroscopy" Trends in Biotechnology 28(6) 317-323 2010.
Cordero, Eliana, et al., "In-vivo Raman spectroscopy: from basics to applications," J. Biomed Opt. 23(7), 071210 (2018).
Stevens, Oliver, et.al. "Developing fibre optic Raman probes for applications in clinical spectroscopy," Chem. Soc. Rev., (2016) ,45, 1919-1934.
Wang, Jianfeng et al. "Development of a beveled fiber-optic confocal Raman probe for enhancing in vivo epithelial tissue Raman measurements at endoscopy." Optics letters 38 13 (2013): 2321-3.
Motz, Jason et al., "Optical Fiber Probe for Biomedical Raman Spectroscopy," Applied optics. 43 (2004): 542-54.
Derosa Michael, "Photothermal Behavior of an Optical Path Adhesive Used for Photonics Applications at 1550 nm", Applied Optics, vol. 40, No. 36, Dec. 20, 2001, pp. 6611, ISSN 00003-6935.
European Extended Search Report, Application No. 21828985.8, mailed Jun. 11, 2024.

* cited by examiner

INSET

INSET FIG. 7B

METHOD AND APPARATUS FOR FIBER OPTIC PHOTOTHERMAL IMAGING AND SPECTROSCOPY

This application is a National Stage Application of PCT/US2021/039053, filed Jun. 25, 2021, which claims benefit of priority to U.S. Provisional Application No. 63/044,921, filed Jun. 26, 2020, which applications are incorporated herein by reference. To the extent appropriate, a claim of priority is made to each of the above disclosed applications.

TECHNICAL FIELD

Embodiments disclosed herein relate to investigating or analyzing materials by the use of optical systems, i.e. using infrared, visible, or ultraviolet light. Embodiments described herein relate to imaging and spectroscopy, and, more particularly, to enhancements to photothermal imaging and spectroscopy systems and techniques for acquiring spectral information indicative of the optical properties and/or material or chemical composition of a sample, for example, information that correlates to an infrared (IR) absorption spectrum.

BACKGROUND

Fourier Transform Infrared (FTIR) spectroscopy is the most common form of IR spectroscopy. FTIR works by measuring transmission of an infrared light through a sample or reflection of IR light from a sample as a function of wavenumber (a measure of the frequency of the IR light). FTIR based microscopes combine an FTIR spectrometer and microscope optics to provide spatially resolved measurements of IR absorption, transmission, and/or reflection. A fundamental constraint on conventional FTIR microscopy is that it can only achieve spatial resolution on the order of the wavelength of the IR light used. The fundamental limit is determined by optical diffraction and is set by the wavelength of the IR light and the numerical aperture of the IR illumination and/or collection optics. Practical limitations may degrade this spatial resolution further. The spatial resolution of the FTIR microscope is wavelength dependent, but is on the order of 10 microns for wavelengths in the mid-IR. An example of an FTIR spectroscopy approach is shown, for example, in U.S. Pat. No. 7,630,081, which describes recent improvements to FTIR interferometers. Conventional FTIR spectroscopy can involve significant sample preparation to ensure appropriate transmission of the mid-IR beam through the sample, which is not practicable or desirable for many opaque, frangible, or biological substances. An example of conventional FTIR spectroscopy techniques used for cancer detection is described in Mark A. Mackanos, et al., "Fiber-optic probes enable cancer detection with FTIR spectroscopy" *Trends in Biotechnology* 28(6) 317-323 2010.

Attenuated Total Reflection (ATR) spectroscopy is based on indirect reflection of a beam through an intervening crystal in direct contact with the sample. ATR spectroscopy can only achieve resolutions on the order of 3 microns using mid-IR beams. ATR spectroscopy necessarily requires direct contact of the intervening crystal with the sample which can cause deformation or breaking of the sample, and requires a significant amount of sample preparation, particularly for organic samples. Furthermore, reflection or refraction between the crystal and the sample requires good contact between the two. If good contact is not established, then the light may reflect or refract based on the refractive index of the material between the sample and the crystal, rather than based on the properties of the sample itself. Both FTIR and ATR suffer from a variety of artifacts that can distort the spectra, including size and shape dependent scattering artifacts and dispersive effects, especially when operated in reflection. These issues can make it very difficult to compare spectra to FTIR library spectra, thus complicating material identification and/or quantification.

Raman spectroscopy is based on illuminating a sample with a narrow band laser source and measuring the spectrum of wavelength shift light that scatters from the illuminated area. Conventional Raman spectroscopy typically utilizes a visible laser source (e.g. 532 nm or 633 nm), and sometimes utilizes a near-IR light source (e.g., 785 nm or 1064 nm), but does not utilize a mid-IR light source (e.g., more than 2500 nm). Wavelengths longer than 1064 nm are generally not used as Raman excitation sources because Raman sensitivity decreases like the 4th power of the excitation wavelength as well as diminished sensitivity of camera-based detectors for longer wave excitation.) An early example of a Raman spectroscopy approach is shown, for example, in U.S. Pat. No. 2,940,355. Although Raman spectroscopy can achieve resolutions down to several hundred nanometers, it also has limitations, including sample fluorescence and much smaller spectral libraries than infrared.

Fiber optics work by transmitting light along the interior of an optically transparent fiber core, usually surrounded by a cladding material. (Optics, $4^{th}$ Ed.; Eugene Hecht, Pearson, 2002.) The fiber core and cladding generally have a difference in index of refraction (or a gradient in index at the boundary) to radially confine the light. In some cases, the fibers may be hollow core, i.e. the core comprises air or vacuum. Conventionally, more than one fiber is combined into a larger structure referred to as a "bundle." The bundle may be made of fibers comprising a single material type or may be made of fibers with more than one material type. Bifurcated fibers, or bundles, have two or more fibers side-by-side in the common end and break out into two or more branches at the other end. The fiber type used in each branch can be the same or different, allowing optimization of the fiber size, or range of light wavelength, depending on the application.

Examples of Raman spectroscopy using fiber probe detection for in vivo application are described, for example, in Cordero, Eliana, et. al, "In-vivo Raman spectroscopy: from basics to applications," *J. Biomed. Opt.* 23(7), 071210 (2018); Stevens, Oliver, et.al. "Developing fibre optic Raman probes for applications in clinical spectroscopy," *Chem. Soc. Rev.*, (2016),45, 1919-1934; Wang, Jianfeng et al. "Development of a beveled fiber-optic confocal Raman probe for enhancing in vivo epithelial tissue Raman measurements at endoscopy." *Optics letters* 38 13 (2013): 2321-3; and Motz, Jason et. al., "Optical Fiber Probe for Biomedical Raman Spectroscopy," *Applied optics*. 43 (2004): 542-54.

U.S. Publ. Appl. No. 2017/0146455A1 describes an approach for a non-invasive substance analysis with light, such as infrared light, in which an intermediary optical medium is used for the light to be emitted through toward a sample.

U.S. Pat. No. 9,091,594 describes an alternative non-destructive approach for photothermal spectroscopy for chemical spectroscopy and imaging that uses two beams of light of differing wavelengths to achieve sub-micron spatial resolution, but in a non-contact manner and without the onerous sample preparation requirements associated with ATR or FTIR techniques described above. One method described in that patent includes illuminating a sample with a first beam of IR light having a wavelength of at least 2.5 microns to create a photothermal change in a region within the sample due to absorption of energy from the first beam, and then illuminating at least a portion of the region within the sample with a second beam of light having a wavelength of less than 2.5 microns to detect the photothermal change in the region at a resolution smaller than a diffraction limit of the first beam. Although the alternative dual beam photothermal spectroscopy technique described in U.S. Pat. No. 9,091,594 provides significant advantages over the three general approaches to mid-IR spectroscopy and imaging, further enhancements and improvements to this new photothermal technique are desirable.

A key limitation of current FTIR techniques is the ability to access the sample of interest. Conventional FTIR relies on mounting a sample of interest on a plate, crystal, or within a transmission cell. However, many samples of interest are in locations that are inaccessible to a benchtop FTIR system or cannot be removed from the environment for analysis. For example, it may be difficult to access biological specimens for analysis without removing a sample and potentially altering or disturbing the integrity of that sample Similarly, analysis of archeological artifacts, fine art, antiquities, and forensic samples require samples to be kept intact and prohibit or discourage removal of a sample to a plate mount, as would be done in conventional FTIR. Therefore, improvements in the means and techniques for how spectroscopy can access and analyze these kinds samples in the constraints of the normal environment would be advantageous.

SUMMARY

Various embodiments are described for performing chemical spectroscopy on samples, including biological and in vivo samples, using a multifunctional platform that uses a dual beam fiber optic system that can provide the following benefits: (1) up to 10× better spatial resolution than conventional IR fiber probes; (2) elimination of scattering and dispersive artifacts common in conventional reflection mode IR spectroscopy; and/or (3) simultaneous multi-functional measurements for example combining infrared spectroscopy, Raman spectroscopy, and fluorescence detection. In embodiments described herein, at least two separate light beams of a dual-beam system are used for excitation and sensing.

The dual-beam system as described in various embodiments can include at least a first light beam of infrared radiation for exciting molecular resonances in the sample that results in local heating from absorbed IR radiation and a separate second light beam for probing the local heating from the absorbed IR radiation. The first IR beam is generally either a tunable IR source and/or a broadband source such that it can excite a plurality of molecular resonance of a sample. The second probe beam is generally a fixed wavelength source and generally has a wavelength shorter than the first beam. The second probe beam allows measurements of infrared spectra with higher spatial resolution and avoiding artifacts common in conventional IR spectroscopy. In various embodiments, these light beams can be arranged in parallel optical fibers, or arranged within a single optical fiber, and these two different beams may be spatially distinct from one another or may be distinguished by different wavelengths.

In various embodiments, the probe beam can sense a temperature rise in the sample resulting from IR absorption by sensing one or more changes in the sample resulting from the heat, for example deformation, expansion, and/or change in index of refraction of a sample. In some embodiments, the probing/sensing beam can also detect properties of the sample, such as by Raman spectroscopy, fluorescence, or combinations of those techniques. The measurement of Raman spectroscopy and/or fluorescence detection can be both simultaneous and collocated with the measurement of IR absorption, providing a rich set of data for multi-modal chemical analysis.

In various embodiments of a dual-beam photothermal spectroscopy system, a sample region is illuminated by the excitation light beam and the resulting photothermal response due to infrared absorption is read out with the probe light beam. The photothermal response is measured as a function of the wavelength (or equivalently wavenumber) of the infrared light source to construct a spectrum that is indicative of the sample composition. Because the probe beam is generally fixed wavelength, it avoids wavelength dependent dispersive effects and size and shape scattering effects common in conventional IR spectroscopy. Even if a portion of the probe beam light is scattered, this scattering is constant as a function of the IR excitation wavelength. Thus, the dual beam fiber system can collect high quality IR spectra that can readily be used for sample identification, characterization and quantification.

In embodiments, the measurements collected by these two light beams operating in coordination with one another contains more data and can be collected at a higher resolution than operating the beams independently from one another. That is, the probing/sensing light beam has a more precise spatial resolution than the heating/infrared light beam due to its lower Abbe diffraction limit, whereas the heating/infrared light beam can initiate spectroscopy data or wavelength shifts due to a photothermal response that would not be caused by a sensing light beam operating in isolation.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 7B shows an enlarged view of the encircled region of FIG. 7A.

DETAILED DESCRIPTION

Definitions

Figure 1A:
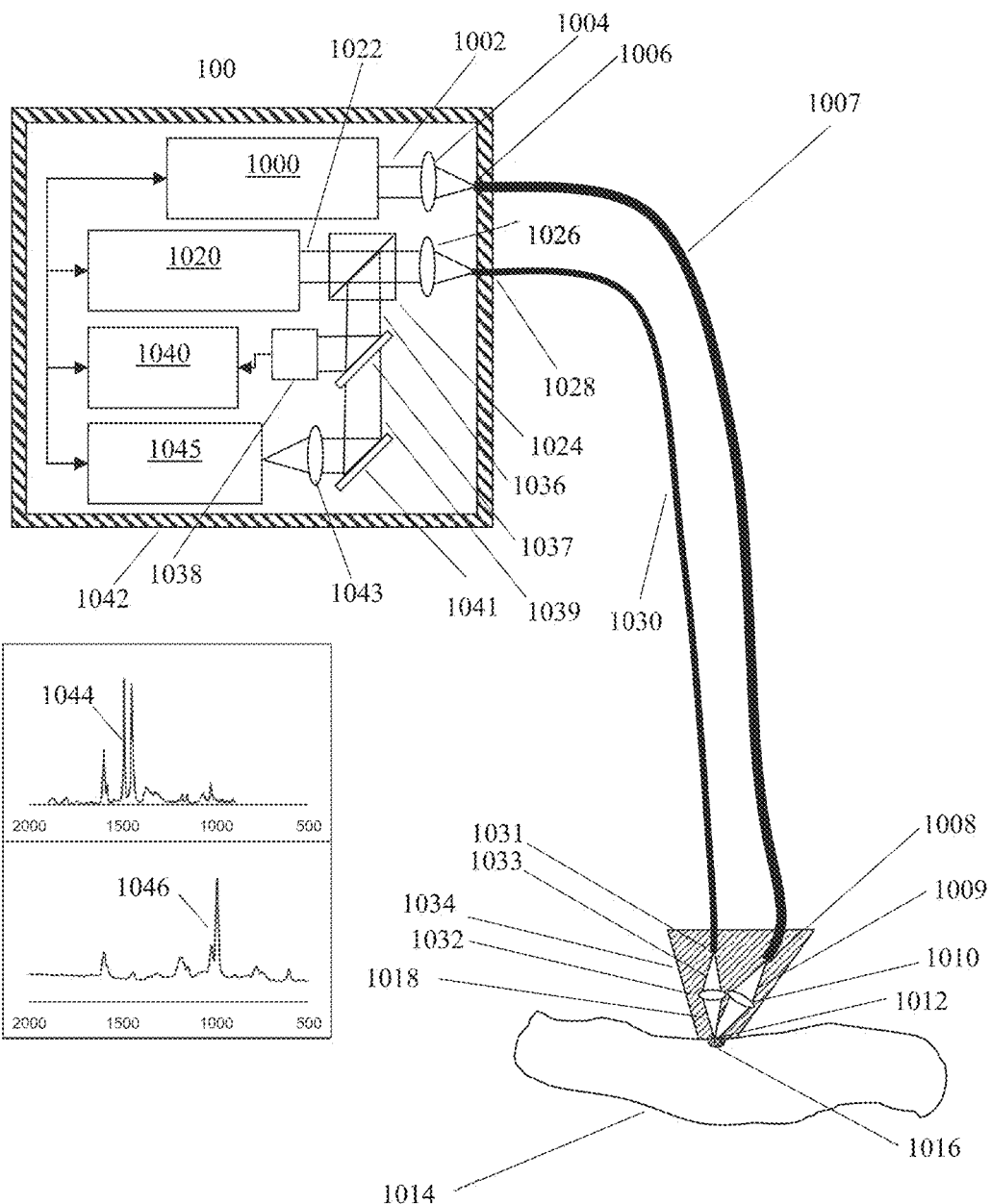
FIG. 1A is a conceptual simplified internal block diagram of a dual beam fiber optic probe system having capability to perform infrared spectroscopy.

For purposes of this specification, the following terms are specifically defined as follows:

An "analyzer/controller" refers to a system to facilitate data acquisition and control of the dual probe system. The analyzer/controller may be a single integrated electronic enclosure or may comprise multiple distributed elements. The control elements may provide control for positioning and/or scanning of the fiber probe and/or sample. They may also collect data about the probe beam deflection, motion or other response, provide control over the excitation and/or probe power, polarization, steering, focus and/or other functions. The control elements etc. may include a computer program method or a digital logic method and may be implemented using any combination of a variety of computing devices (computers, Personal Electronic Devices), analog and/or digital discrete circuit components (transistors, resistors, capacitors, inductors, diodes, etc.), programmable logic, microprocessors, microcontrollers, application-specific integrated circuits, or other circuit elements. A memory configured to store computer programs may be implemented along with discrete circuit components to carry out one or more of the processes described herein.

"Beam combiner" means an optical element that can combine two beams onto the same optical path. In one configuration, a beam combiner may be a beam splitter used in a reverse direction, i.e. combining one beam that reflects off of the beam splitter interface with another beam that is transmitted through the beam splitter interface. A beam splitter cube, for example, can be used as both a beam splitter and a beam combiner. Optical elements that are marketed as beam splitters can be used as a beam combiner, even if they are not used to split light onto two paths. For example, a Mach-Zehnder interferometer uses one beam splitter to split incident light onto two paths and a second beam splitter to recombine the two beams. In this case, the second beam splitter is being used as a beam combiner. In a Michelson interferometer, a single beam splitter is used to both divide the incident light and then recombine it. Thus, the beam splitter in a Michelson interferometer as being used as both a beam splitter and a beam combiner. A beam combiner can also be an optical fiber-based device, for example combining the light from two input fibers into one output fiber, for example a 1×2 fiber coupler. A single 1×2 fiber coupler can be used as both a beam splitter and a beam combiner.

"Beam splitter" refers to an optical element that can divide light onto at least two paths. A beam splitter can comprise a plate, a cube and/or a prism or other shapes/configurations that can divide a beam of light. The beam splitter can comprise a thin film that is partially reflecting at the wavelength of interest such that a portion of an incident beam is reflected and another portion is transmitted. A beam splitter may be polarizing, wherein in substantially transmits light of one polarization and reflects light of an orthogonal polarization. A beam splitter may also divide light along two transmission paths based on polarization, for example in the case that the beam splitter is a Nomarski or Wollaston prism. A beam splitter may also be non-polarizing, where light is divided between two paths without substantial dependence on the polarization of the incident light. A beam splitter can also be an optical fiber-based device, for example splitting light from one input optical fiber into at least two output optical fibers, for example a 1×2 fiber coupler. A beam splitter may be a 50:50 beam splitter in which substantially equal fractions of light are directed on two different paths. They can also be unbalanced, for example a 90:10 or 70:30 or similar beam splitter that direction 90% of light on one path and 10% on another, or 70% on one path and 30% on another.

A "camera" refers to an array-based photodetector comprising a plurality of photosensitive pixels. A camera may comprise one or more technology including but not limited to CCD, EM-CCD, CMOS, s-CMOS, and/or other photosensitive array technologies. The camera may support frame rates from a few frames per seconds, hundreds of frames per second, or even thousands of frames per second or higher. Alternatively, a camera may include other approaches for detecting spatial resolution and relationship of objects/pixels of a scene, including motion sensors or indexing fiducials.

"Collecting probe light," "Collecting probe radiation" refer to collecting radiation of a probe light beam that has interacted with a sample. The probe light can be collected after reflection, scattering, transmission, evanescent wave coupling, and/or transmission through an aperture probe.

"Collimating optic" refers to any of the above optical elements arranged in a way to generally collimate radiation. In some embodiments the same optic(s) may serve as both a focusing optic and a collimating optic, for example focusing light in one direction of propagation and then recollimating the light in the opposite direction of propagation.

"Confocal microscopy" refers to a form of optical microscopy in which the light collected at a detector is confined to light that passes through a small volume within the 3D focus volume of an optical objective on a sample. Confocal microscopy is often performed by placing a "confocal aperture" at a focal plane that is equivalent with the focal plane of the sample, thus blocking stray light that does not pass through the focus volume on the sample.

A "detector" refers to a device that produces a signal indicative of the power, intensity and/or energy of light/radiation incident on the detector surface. The signal will generally be an electrical signal, for example a voltage, current and/or an electrical charge. The detector may be a photodiode, a phototransistor, a charge coupled device (CCD). In some cases, a detector may be a semiconducting detector, for example a silicon PIN photodiode. A detector may also be an avalanche photodiode, a photomultiplier tube, or any other device that produce a change in current, voltage, charge, conductivity or similar upon incidence of light. A detector may comprise a single element, multiple detector elements, for example a bi-cell or quad-cell, a linear or two-dimensional array of detector elements, including camera-based detectors.

"Diffraction limit" of a light beam means the minimum separation of two optical sources that can be distinguished by a detector. The Abbe diffraction limit d for a microscope having a numerical aperture NA and operating at a wavelength λ is defined as $d=\lambda/(2 \cdot NA)$. Physical restraints on the numerical aperture of a microscope prohibit very large numerical apertures, and therefore the diffraction limit of a microscope depends strongly upon the operating wavelength used for detection, with large wavelengths corresponding to relatively poor resolution and high wavelengths corresponding to increased precision.

"Demodulate" or "demodulation" refers to extracting an information-bearing signal from an overall signal, usually, but not necessarily at a specific frequency. For example, in this application, the collected probe light collected at a photo detector represents an overall signal. The demodulation process picks out the portion that is being perturbed by infrared light absorbed by the sample. Demodulation can be accomplished by a lock-in amplifier, a fast Fourier transform (FFT), a calculation of a discrete Fourier component at a desired frequency, a resonant amplifier, a narrow band bandpass filter, or any other technique that largely enhances the signal of interest while suppressing background and noise signals that are not in sync with the modulation.

A "demodulator" refers to a device or system that performs demodulation.

"Figure of merit" refers to any metric or indicator of the relative quality of a signal or measurement. The figure of merit can for example be a measurement sensitivity, a signal strength, a noise level, a signal to noise ratio, a background level, a signal to background ratio, any combination of these, or other metric that lets one rank the relative quality of a signal and/or measurement.

"Focusing optic" refers to one or more optical elements with the ability to focus light. A focusing optic can comprise one or more refractive lenses, curved mirrors, diffractive optics, Fresnel lenses, volume hologram, metamaterial, or any combination thereof or any other device or component capable of focusing radiation.

"Fluorescence" refers to the emission of light from a sample at one wavelength due to excitation at another wavelength due to fluorescent excitation and emission processes.

"Illuminate," "Illuminating," and "Illumination" mean to direct radiation at an object, for example a surface of a sample, the probe tip, and/or the region of probe-sample interaction. Illumination may include radiation in the infrared wavelength range, visible, and other wavelengths from ultraviolet to a millimeter or more. Illumination may include any arbitrary configuration of radiation sources, reflecting elements, focusing elements and any other beam steering or conditioning elements.

"Infrared absorption spectrum" refers to a spectrum that is proportional to the wavelength dependence of the infrared absorption coefficient, absorbance, or similar indication of IR absorption properties of a sample. An example of an infrared absorption spectrum is the absorption measurement produced by a Fourier Transform Infrared spectrometer (FTIR), i.e. an FTIR absorption spectrum. In general, infrared light will either be absorbed (i.e., a part of the infrared absorption spectrum), transmitted (i.e., a part of the infrared transmission spectrum), or reflected. Reflected or transmitted spectra of a collected probe light can have a different intensity at each wavelength as compared to the intensity at that wavelength in the probe light source. It is noted that a IR measurements are often plotted showing the amount of transmitted light as an alternative to showing the amount of light absorbed. For the purposes of this definition, IR transmission spectra and IR absorption spectra are considered equivalent as the two data sets as there is a simple relationship between the two measurements.

"Infrared source" and "source of infrared radiation" refer to one or more optical sources that generates or emits radiation in the infrared wavelength range, generally between 2-25 microns. The radiation source may be one of a large number of sources, including thermal or Globar sources, supercontinuum laser sources, frequency combs, difference frequency generators, sum frequency generators, harmonic generators, optical parametric oscillators (OPOs), optical parametric generators (OPGs), quantum cascade lasers (QCLs), interband cavity lasers (ICLs), synchrotron infrared radiation sources, nanosecond, picosecond, femtosecond and attosecond laser systems, CO2 lasers, microscopic heaters, electrically or chemically generated sparks, and/or any other source that produces emission of infrared radiation. The source emits infrared radiation in a preferred embodiment, but it can also emit in other wavelength ranges, for example from ultraviolet to THz. The source may be narrowband, for example with a spectral width of <10 cm$^{-1}$ or <1 cm$^{-1}$ less, or may be broadband, for example with a spectral width of >10 cm$^{-1}$, >100 cm$^{-1}$ or greater than 500 cm$^{-1}$. Broadband sources can be made narrow band with filters, monochromators and other devices. The infrared source can also be made up of one of discrete emission lines, e.g. tuned to specific absorption bands of target species.

"Interacting" in the context of interacting with a sample means that light illuminating a sample is at least one of scattered, refracted, absorbed, aberrated, diverted, diffracted, transmitted, and reflected by, through and/or from the sample.

A "lock-in amplifier" is one example of a "demodulator" (defined above) and is a device, system, and/or an algorithm that demodulates the response of a system at one of more reference frequencies. Lock-in amplifiers may be electronic assemblies that comprise analog electronics, digital electronics, and combinations of the two. They may also be computational algorithms implemented on digital electronic devices like microprocessors, field programmable gate arrays (FPGAs), digital signal processors, and personal computers. A lock-in amplifier can produce signals indicative of various metrics of an oscillatory system, including amplitude, phase, in phase (X) and quadrature (Y) components or any combination of the above. The lock-in amplifier in this context can also produce such measurements at both the reference frequencies, higher harmonics of the reference frequencies, and/or sideband frequencies of the reference frequencies.

"Modulating" or "modulation" when referring to radiation incident on a sample refers to changing the infrared laser intensity at a location periodically. Modulating the light beam intensity can be achieved by means of mechanical chopping of the beam, controlled laser pulsing, and/or deflecting the laser beam, for example by a tilting mirror that is driven electrostatically, electromagnetically, with piezo actuators or other means to tilt or deform the mirror, or high speed rotating mirror devices. Modulation can also be accomplished with devices that provide time varying transmission like acousto-optic modulators, electro-optic modulators, photo-elastic modulators, pockel cells, and the like. Modulation can also be accomplished with diffraction effects, for example by diffractive MEMS-based modulators, or by high speed shutters, attenuators, or other mechanisms that change the intensity, angle, and/or phase of the laser intensity incident on the sample.

"Near infrared light" generally refers to a wavelength range of infrared (IR) light corresponding to 0.75-2 µm.

A "narrowband light source" a light source with a narrow bandwidth or linewidth, for example a light of linewidth smaller than 8 cm-1, but in general it can be a light source with a linewidth narrow enough that the linewidth does not cover a spectral range of interest of the sample.

"Optical property" refers to an optical property of a sample, including but not limited to index of refraction, absorption coefficient, reflectivity, absorptivity, real and/or imaginary components of the index refraction, real and/or imaginary components of the sample dielectric function and/or any property that is mathematically derivable from one or more of these optical properties.

"Optical response" refers to the result of interaction of radiation with a sample. The optical response is related to one or more optical properties defined above. The optical response can be an absorption of radiation, a temperature increase, a thermal expansion, a photo-induced force, the reflection and/or scattering of light or other response of a material due to the interaction with illuminating radiation.

"Photothermal distortion" refers to a change in the properties of a sample due to absorption of optical energy, for example the absorption of IR radiation. The photothermal distortion may refer to a change in index of refraction, reflectivity, thermal expansion, surface distortion, or other effects that can be detected with a probe beam.

A "probe source," "probe light source," or "probe radiation source" refer to a radiation source that can be used for sensing of an optical property of a sample. A probe light source can be used to sense the response of the sample to the incidence of light from the infrared light source. The radiation source may comprise a gas laser, a laser diode, a superluminescent diode (SLD), a near infrared laser, a UV and/or visible laser beam generated via sum frequency or difference frequency generation, for example. It may also comprise any or other sources of near-infrared, UV, and/or visible light that can be focused to a spot on the scale smaller than 2.5 micrometer, and or even smaller than 1 micrometer, and possibly smaller than 0.5 micrometer. In some embodiments, the probe light source may operate at a wavelength that is outside the tuning or emission range of the infrared light source, but the probe light source can also be a fixed wavelength source at a select wavelength that does in fact overlap with the tuning range of the infrared light source. A "probe light beam" or "sensing light beam" is a beam originally emitted from a probe light source.

"Probe beam" is a beam of light or radiation that is directed onto a sample to detect a photothermal distortion or other optical change resulting from the interaction of IR radiation with the sample, for example to detect the absorption of IR radiation by the sample.

"Raman" refers to light that is inelastically scattered from a sample at one or more wavelengths that are different from the excitation wavelength due to Raman scattering. "Raman spectroscopy" refers to measuring the spectroscopic content (Raman spectra) of Raman scattered light, for example the intensity of Raman scattered light as a function of Raman shift. "Raman spectrometer" is a device for examining Raman shifts in light collected from a sample and producing Raman spectra and/or Raman images.

A "retarder" refers to an optical element that induces a relative optical phase delay in an optical path. Examples of retarders are wave plates, for example half wave plates, quarter wave plates and eight wave plates. One or more retarders/wave plates can be used to introduce an optical phase difference between two polarizations of light, for example to introduce a phase difference between two paths of a quadrature interferometer.

"Signal indicative of" refers to a signal that is mathematically related to a property of interest. The signal may be an analog signal, a digital signal, and/or one or more numbers stored in a computer or other digital electronics. The signal may be a voltage, a current, or any other signal that may be readily transduced and recorded. The signal may be mathematically identical to the property being measured, for example explicitly an absolute phase signal or an absorption coefficient. It may also be a signal that is mathematically related to one or more properties of interest, for example including linear or other scaling, offsets, inversion, or even complex mathematical manipulations.

"Spectrum" refers to a measurement of one or more properties of a sample as a function of wavelength or equivalently (and more commonly) as a function of wavenumber.

The terms "about" or "approximate" and the like are synonymous and are used to indicate that the value modified by the term has an understood range associated with it, where the range can be ±20%, ±15%, ±10%, ±5%, or ±1%.

The term "substantially" is used to indicate that a result (e.g., measurement value) is close to a targeted value, where close can mean, for example, the result is within 80% of the value, within 90% of the value, within 95% of the value, or within 99% of the value.

Embodiments described herein improve upon earlier photothermal characterization systems in that they are uniquely suited to the characterization of wet, fragile, bulky, and otherwise difficult-to-characterize samples. Embodiments can be either benchtop or handheld, further expanding upon their usefulness in environments such as archeological sites, customs stations, or other locations that are either remote or where samples cannot practicably be shipped offsite for analysis at a laboratory.

Dual-Beam Imaging and Spectroscopy

In one embodiment, the current disclosure is directed towards obtaining measurements of optical properties with a fiber optic dual-beam system. The fiber optic dual-beam system includes at least one excitation beam, and at least one probe beam. The excitation and probe beams are directed towards a sample of a specimen or a material and data corresponding to a photothermal effect in that sample is collected at a resolution that is smaller than the diffraction limit of the excitation beam. In embodiments, infrared absorption spectrum of a sample can be sensed with sub-micron scale resolution, and in some embodiments additional, complementary measurement techniques can also be used simultaneously or in parallel.

FIG. 1A shows a conceptual simplified internal block diagram of a dual beam fiber optic probe system 100 having capability to perform infrared spectroscopy. IR radiation source 1000 emits a beam of IR radiation 1002 that is optionally focused by focusing element 1004 (e.g. a lens or reflective focusing element) onto the proximal end 1006 of first optical fiber 1007. IR radiation travels through the fiber to the distal end 1008 where a beam of IR radiation 1009, sometimes referred to as a pump beam, is re-emitted from the fiber. This radiation is optionally refocused to the sample with a focusing optic 1010 onto a region 1012 of sample 1014.

If the IR source 1000 is tuned to an absorbing wavelength of sample region 1012, IR absorbing areas will heat up slightly, resulting in a localized hot spot 1016. The temperature increases within hot spot 1016 are indicative of the IR absorption properties of the region 1012 of the sample, which in turn may be used to analyze various aspects of the materials of the region 1012. In embodiments, the relative temperature increases due to IR absorption are read out with a separate probe beam 1018. The wavelength of the probe beam 1018 is generally selected to be shorter than the wavelength(s) of IR the IR beam 1009, thus the probe beam can be focused to a smaller spot size. For example, if the IR radiation is at 5.32 um and the probe radiation is at 532 nm, the probe beam can be focused to a spot size roughly 10× smaller than the IR beam. The probe beam can sense changes thermal expansion, surface deformation, surface shape and/or changes in index of refraction associated with the IR absorption induced temperature change.

In embodiments, the probe beam 1018 originates at probe beam source 1020, typically within the same enclosure 1042 as the IR radiation source 1000. Probe beam source 1020 emits a beam of probe radiation 1022 that is optionally passed through a beam splitter 1036. At least a portion of the probe beam passes through the beam splitter 1024 and is coupled into the proximal end 1028 of second fiber 1030 using a focus element 1026, typically a lens. Probe radiation travels through fiber 1030 until it exits at the distal end 1031 of the second fiber. In embodiments, the probe radiation 1033 is optionally refocused with a focusing element 1032 onto region of sample 1014 that at least partially overlaps the IR illuminated region 1016. In some configurations focusing elements 1010 and 1032 can be the same shared optic. The arrangement shown, however, can be an advantageous arrangement in the case that refractive optics are used because many optical materials can have substantially different transmission properties and refractive indices for IR and visible wavelengths. The approach of FIG. 1A thus allows separate optimization of the best focusing optic for IR and for probe wavelengths and can lead to overall smaller focused spot sizes and improved optical fluence at the sample.

Probe light that is reflected and/or scattered from sample 1014 is recollected by the distal end of fiber 1030. Alternately, the light can be recollected with other collection optics and/or one or more additional fibers not shown in this figure but described with respect to other figures. Collected probe radiation that travels back up fiber 1030 re-emerges from the proximal end 1028 of fiber 1030 and is optionally recollimated by focusing element 1026. When the collected probe light strikes beam splitter 1024, at least a portion 1036 of the collected probe light is directed downwards toward the probe beam detection section. The probe light portion 1036 then impinges on an optional dichroic 1037 that directs light at the probe wavelength to detector 1038. A signal indicative of the amount of light striking detector 1038 is directed to analyzer/controller 1040. Analyzer/controller 1040 then analyzes the detector signal to determine an amplitude of modulation of the detector signal in response to IR absorption by the sample.

In embodiments as described, IR absorbing regions of the sample 1016 will heat up in response to absorbed IR light. This thermal change is then read out by monitoring changes in the probe light reflected and/or scattered from the IR absorbing regions of the sample. The scattered/reflected probe light can be captured by the focusing optic, e.g. a ball lens and then recoupled into the probe fiber 1008 for detection and analysis. Alternately, and as described in more detail with respect to other figures, the collected probe light can be captured by auxiliary collection fibers. A variety of other endpiece configurations will be described associated with FIGS. 2A-2B and 3A-3C.

For improved signal to noise, it may be desirable to analyze the change in collected probe beam power synchronously with the IR excitation. For example, IR source 1000 may be a pulsed or other modulated source. The signal from detector 1038 can be demodulated by analyzer 1040 at a frequency that is synchronized with the pulse/modulation frequency of IR source 1000. In embodiments, this can be accomplished by implementing a lock-in amplifier on analyzer 1040 and using the pulse or modulation waveform of IR source 1000 as the reference for the lock-in. This can also be accomplished by comparing the detector signal levels with the IR source on and off. It is also possible to employ a resonant amplifier to amplify the detector signal at a specific frequency corresponding to the modulation frequency of the IR source. The signal from detector 1038 can also be analyzed by a Fourier transform or other frequency domain analysis to isolate an amplitude at the modulation frequency of the IR source.

For the above examples, it is possible to analyze the detector response at the modulation frequency of the IR source and/or at a higher harmonic thereof. In any of these cases, it may be desirable to extract a signal indicative of the modulation of the probe beam detector signal in response to IR absorption by the sample. The detected modulation may be an RMS amplitude, a peak-to-peak amplitude, a phase difference or any suitable measure of a difference in collected light resulting from IR absorption. An IR absorption spectrum 1044 of the region of the sample illuminated by the probe beam can be constructed by measuring the modulation of collected probe beam as a function of wavelength (or wavenumber) of IR source 1000.

In embodiments, the IR absorption spectra measured has several significant advantages over prior conventional fiber based infrared spectroscopy systems. First, the spatial resolution is determined by the size of the probe beam, not the size of the IR beam. Using a shorter wavelength for the probe beam, the probe beam 1018 can be focused to a spot at the sample that is ~10× smaller than the IR beam illuminated region 1012. Second, this approach avoids size and shape dependent scattering artifacts that influence conventional IR spectra. In a conventional IR spectrometer, the IR absorption is inferred by measuring the amount of IR light that is collected after interacting with the sample. But scattering events in the sample can greatly impact the amount of IR light that is collected, leading to excessive artifacts and making interpretation of the spectra difficult. In embodiments, the IR absorption is inferred by measuring changes in the collected probe beam, not the IR beam. So, the IR absorption spectra measured with the probe beam are substantially immune to these IR scattering artifacts. The approach also avoids dispersive artifacts. In conventional IR spectroscopy performed in reflection, the amount of IR light reflected from the sample depends both on the absorption coefficient and on the real index of refraction which is known to change significantly near IR absorption peaks. The result is that the location and shape of IR absorption peaks can become distorted in conventional IR spectrometers, making analysis, identification and quantification difficult. The various embodiments this problem is overcome because it is substantially only sensitive to the absorption coefficient. The reason is that the probe beam measures detects the effect of local sample heating from the absorption of IR light. So, the photothermal detection directly probes the IR absorption, while being substantially insensitive to changes in the real index of refraction. Thus, the IR absorption spectra measured by the current technique provide better correlation to conventional transmission FTIR measurements, thereby providing more robust data for chemical analysis.

The apparatus of FIG. 1A can also perform simultaneous Raman spectroscopy. In embodiments, the apparatus will also quantify the Raman scattered light that results at the sample 1014 where probe light interacts with the sample. In addition to being able to sense thermal changes in the sample, the probe beam is also able to probe molecular resonances that give rise to Raman scattering. When Raman scattering occurs a portion of the probe light is shifted to higher and/or lower wavelengths. By obtaining a spectrum of the wavelength shifted light, one can infer information about the molecular resonance of the sample. Because of different selection rules, IR and Raman measurements are often complementary. In fact, vibrational bands that are strong Raman scatterers are often weak IR absorbers and vice versa. Therefore, the ability to measure both Raman and IR spectra in the same sample provides a significant benefit.

To perform simultaneous IR and Raman spectroscopy, probe light collected from the sample is divided onto two paths, one analyzed for IR absorption as described above and the path other for Raman scattering. The probe light is divided onto two paths by dichroic 1037. In the configuration show, dichroic 1037 is selected to reflect the original probe beam wavelength towards detector 1038 and then transmit wavelength shifted light, i.e. probe light where Raman scattering has occurred. The Raman shifted light beam 1039 is optionally directed to one or more steering mirrors 1041 and then to focusing optic 1043 which focuses the Raman shifted light onto the entrance port of Raman spectrometer 1045. Alternatively, focusing optic 1043 can focus the Raman shifted light 1039 to an additional fiber coupler to couple the Raman light to an external Raman spectrometer (not shown). Raman spectrometer 1045 analyzes the wavelength content of the Raman shifted light, e.g. the number of detector counts over a plurality of wavelengths (corresponding to a plurality of Raman shift values) to create a Raman spectrum 1046 of the region of sample 1014 illuminated by the probe beam. This spectrum can also be displayed on the user interface of the device as described associated with the description of FIG. 1B.

The IR absorption spectrum 1044 and/or Raman spectrum 1046 can then be analyzed to determine the chemical content of the region of the sample. The IR spectrum 1044 can also be used to analyze, classify, quantify, identify, and/or discriminate the sample. For example, in the case that the sample is a biological cell or tissue, the IR/Raman spectra 1044/1046 (or a plurality of IR and/or Raman spectra) can be used to classify the cell/tissue type, to determine if it is diseased or healthy, detect the presence of cancer, identify a specific pathogen, detect/quantify metabolites, detect/quantify drug penetration, interaction, efficacy, etc. The dual beam fiber probe system in accordance with various embodiments can also be programmed with reference spectra against which measured spectra can be compared. In some modes of operation, instead of displaying an IR/Raman spectrum, the user interface can display a chemical identification based on a degree of match of the measured spectra to the reference spectra. In embodiments, the unit can also be programmed to detect pass/fail scenarios, i.e. where a material being inspected is sufficiently similar to, or divergent from, a stored reference value.

In various embodiments, the dual beam fiber probe can also measure simultaneous infrared spectra and sample fluorescence. Element 1045 of FIG. 1A can be a fluorescence light detector in addition to or instead of a Raman spectrometer. For example, dichroic 1037 can be selected to transmit one or more wavelengths of wavelength shifted probe radiation, where the wavelength shifting occurs due to fluorescence in the illuminated region of the sample. In this embodiment, element 1045 can be a high sensitivity optical detector that can be used to record the amount of light collected in a desired wavelength band. Element 1045 can also be a multispectral detector comprising one or more additional filters and detectors, e.g. to simultaneously detector fluorescence at multiple wavelengths. As with the Raman measurements, these fluorescence measurements are performed at the same location as the IR spectra because both are measured with the probe beam. It is also possible that element 1045 is a Raman spectrometer as described previously and the spectrometer is used to also (or instead) detect the amount of sample fluorescence at any desired wavelength.

The optical fibers 1007 and 1030 may be made of a variety of materials depending on the specific application requirements. Suitable infrared fibers for mid-IR excitation beam are available from vendors like OptoKnowledge, IRflex, CeramOptecNewport, Thorlabs and other sources. In some embodiments, particular chalcogenide fibers may offer good performance in the 1.5 µm to 6.5 or even 10 µm and polycrystalline/silver halide fibers offer good performance from 4-18 µm. Mid-IR hollow core fibers can offer good transmission over 2-16 µm. Many choices are also available for the probe fiber, depending on the probe wavelength selected and the desired illumination area at the sample. Typical optical fibers for the visible wavelengths comprise a silica core, glass and plastic. A suitable fiber for the probe beam can SM400 or SM450 single mode fiber from Thorlabs or similar fiber from other vendors. Some fibers can provide transmission of both the IR and probe beam in a single fiber. For example, zirconium fluoride fibers provide transmission over 285 nm to 4.5 µm. Indium fluoride has transmission from 310 nm to 5.5 µm. This type of fiber for example would support transmission of mid-IR emission, for example, from a periodically poled lithium niobate optical parametric oscillator (emission in the range of 2.5-4 µm) along with a probe beam with wavelengths in the UV, visible, or near IR.

IR source 1000 may comprise quantum cascade laser (QCLs), interband cascade lasers (ICL), optical parametric oscillators (OPO), fiber lasers, supercontinuum sources, femtosecond sources, thermal sources like globars or any other source of IR radiation. One particular source that is miniaturized QCLs, for example one or more "mini-QCL" modules from Block Engineering. Probe beam source 1020 can be a gas laser, a laser diode, a diode pumped solid state laser, a nanosecond, picosecond or femtosecond pulsed laser, a light emitting diode, a superluminescent diode, an incandescent light source, a mercury vapor lamp, a halogen lamp or any other UV, visible, or near-IR light source capable of being launched into an optical fiber. The probe beam source may be continuous wave (CW), chopped, modulated and/or pulsed.

The distal end 1008 of the fiber probe may be optionally mounted in an endpiece 1034. The end piece may provide mounting for focusing optics 1010 and 1032 and optional releasable connections for fibers 1007 and 1030. The endpiece may also be ergonomically shaped to be comfortably held by a human hand and/or may have provisions for mounting in a motorized and/or robotic mechanism for being automatically translated over a sample to measure at specified locations. The endpiece may also be sized such that when the endpiece is touched to a sample the IR and probe beams are overlapped and substantially in focus. Several other configurations of the distal ends of IR and probe fibers will be described later.

The detector, such as element 1045, may be a semiconducting photodiode, for example a silicon PIN photodiode, an avalanche photodiode, a photomultiplier tube, or any other device that produce a change in current, voltage, charge, conductivity or similar upon incidence of light. A detector may comprise a single element, multiple detector elements, for example a bi-cell or quad-cell, a linear or two-dimensional array of detector elements, including camera-based detectors. The detector signal may be amplified using current and/or voltage amplifiers and then sent to analyzing electronics, for example, a demodulator or lock-in amplifier. The output of the pump beam source 1000 can be modulated and/or pulsed using an internal or external pulse control.

Because the collected probe beam signal is demodulated at a frequency corresponding to the modulation of the pump beam, the demodulation signal can be indicative of the degree of deviation of the probe beam induced by the absorption of the pump beam at the sample. The demodulation signal is indicative of the IR absorption by the sample region where the probe beam is focused. The demodulation signal can therefore be used to map pump or other heating beam absorption of the sample on spatial resolution scales smaller than the diffraction limit of the pump beam.

The demodulation signal can be measured at a plurality of wavelengths (or equivalently wavenumbers) corresponding to the IR excitation beam source 1000 to obtain a signal 1044 that is indicative of an infrared absorption spectrum of the region of the sample 1012. These absorption spectra can be measured at a plurality of locations on the sample 1014, translating the sample relative to the focused pump and probe beams, for example by moving the sample with a sample stage, or by moving the fiber optic distal ends, e.g. by moving end piece 1034. In certain embodiments, additional scan lenses or other optics may be desirable for example to raster the positions of the IR and probe beam foci on the sample. Measuring a signal at a plurality of locations produces a family of spectra that can represent the chemical/spectroscopic variation in the sample.

The spectra can be analyzed to produce chemical images that show the distribution of difference chemical species in the sample. Chemical images can also be obtained by mapping the demodulation signal at a fixed wavelength/wavenumber over a plurality of points on the sample. For example, the pump source can be tuned to a wavelength where at least one chemical component in the sample absorbs. Creating a map of the demodulation signal at this fixed wavelength as a function of position on the sample can create a map of the distribution of the absorbing component. Chemical images can be created by tuning the pump source to a single wavelength and scanning over a plurality of locations of the sample and/or by measure pump absorption spectra at a plurality of positions on the sample and then analyzing the absorption at a single wavelength or over a range of wavelengths. Additional chemometric and multivariate analysis techniques can be applied to the family of sensed spectra to produce alternate compositional maps/chemical images.

In embodiments, position tracking devices may be used to monitor the position of the distal end of the fiber probe. For example, 3D localization technologies can be used to record the position and orientation of the fiber probe as a function of time and this data can be synchronized with spectroscopic measurements of the sample to create spatially resolved maps, even if the fiber probe is handheld and moved by a user. For example, optical trackers from PS-Tech using near IR illumination and stereoscopic sensing can provide suitable 3D localization with rates up to 200 Hz, sufficient for capturing motion from a hand scanned fiber probe.

Although in some embodiments, the components of fiber probe 100 inside of enclosure 1042 are illustrated as being arranged in a single plane, it is possible to stack components in a 3D configuration to make more efficient use of space. For example, analyzer/controller 1040 may be mounted instead above or below the IR and probe source, or on a side wall of the enclosure 1042. Additionally, at least one of the detector 1038 or Raman spectrometer 1045 may be mounted on a different level than the IR/probe sources, e.g. on a plane above or below the IR and probe sources. These are just a few examples of how the dual beam fiber probe 100 can use a stacked instead of planar geometry to allow for more efficient miniaturization.

The various embodiments may also include additional light filters, and polarizing lenses, to select and enhance desired wavelengths of light for detection and analysis. For example, a quarter wave plate can be inserted after beam splitter 1024 while the beam splitter 1024 can be selected to be a polarizing beam splitter to provide efficient transmission of probe power into optical fiber 1030 and efficient transmission of returning probe radiation to detector 1038. In this embodiment, it may be desirable to employ a polarization preserving optical fiber for the probe beam.

One advantage of the various embodiments is that IR, Raman, and fluorescence measurements can all be sensed by collection of a single probe beam. As such, it is possible to simultaneously or sequentially collect multiple chemical image maps, for example one map being an image of IR absorption and the other map being a Raman or fluorescence response image. In various embodiments, this makes it possible to obtain simultaneous or sequential measurements of IR absorption, Raman scattering, and/or fluorescence over the same region of the sample (or overlapping regions of the sample) for the purposes of correlative measurements. Furthermore, the measurements described above can optionally be performed in a non-contact mode, and it is not necessary for any physical probe or crystal to create a mechanical contact with the top surface of sample 190. This facilitates rapid, precise measurements that are non-contact and accordingly non-destructive.

Figure 1B:
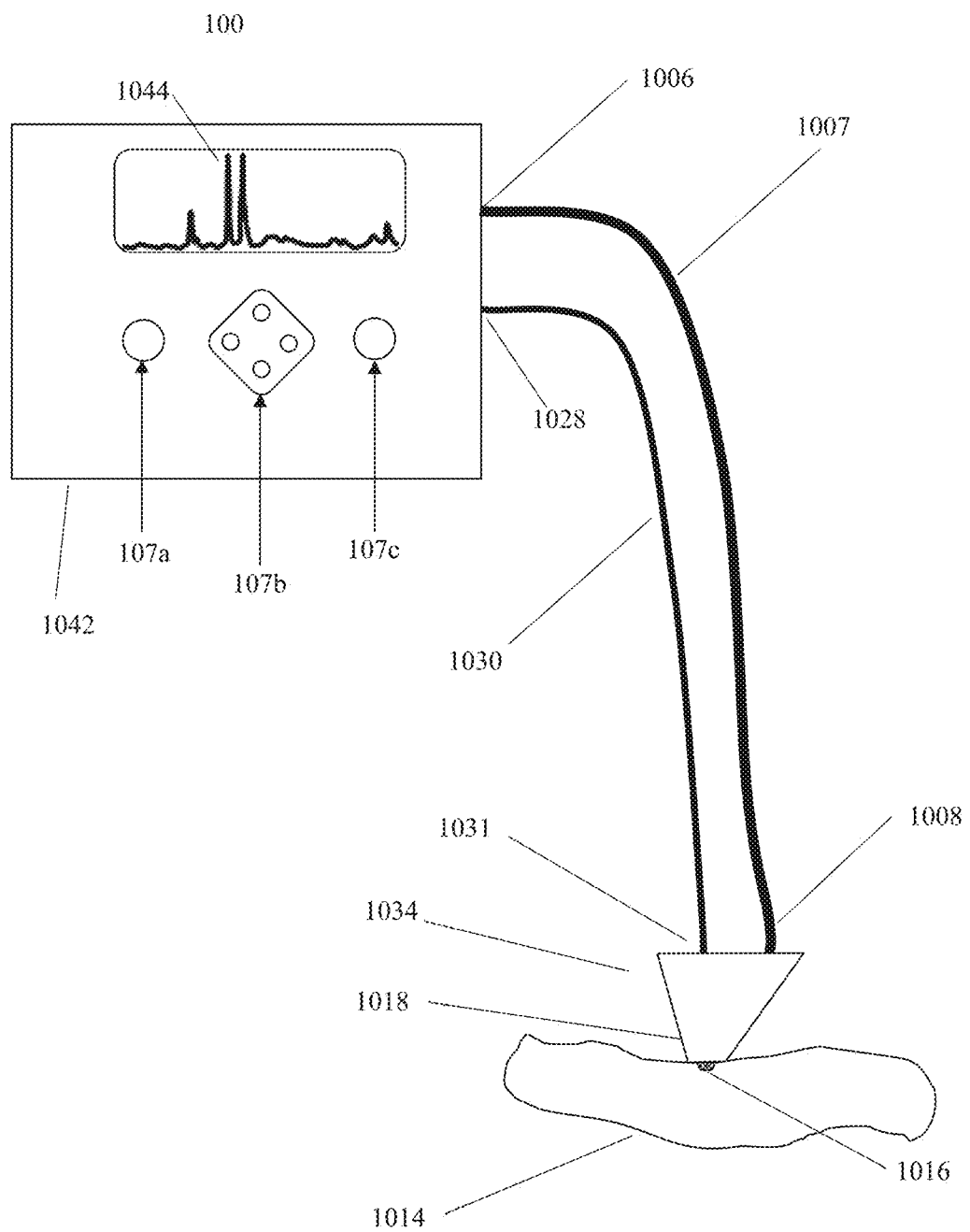
FIG. 1B shows a conceptual simplified external block diagram of the fiber optic probe system of the embodiment of FIG. 1A.

FIG. 1B shows a conceptual simplified external block diagram of the fiber optic embodiment of FIG. 1A. The fiber optic probe system 100 comprises an external housing 1042. In some embodiments, the external housing 1042 is sized for benchtop applications, and in other embodiments, the external housing 1042 is miniaturized and optionally ruggedized for handheld applications. For miniaturized applications, the rugged external housing 1042 may be contoured to the shape of a hand, and may also have ridges, elevations, edges, crests, handles, or other contours to facilitate usage of the fiber optic probe system 100. The rugged external housing 1042 may have one or more ports (not shown) for an external power supply and/or battery charging, and/or ports for connecting/disconnecting one or more fibers. The user interface of the rugged external housing 1042 may have a port for interfacing with a computer or other mobile electronic device or may be operated through an electronic display 106 and control buttons 107 on the user interface. The device may alternately use a touch screen on and/or remote from the device that combines the electronic display and control button functions. The control buttons 107 may have numerous configurations, including a central control button 107*b*, a left-side control button 107*a*, and a right-side control button 107*c*. Control buttons 107 may be circular, square, triangular, or rhombus in shape. The rugged external housing 1042 may also have ports for one or more a fiber optic cables, for example fibers 1007 and 1030. The fibers may be permanently connected through the ports or removable. The fibers may be encased in a one or more ruggedized/protective sheath to protect potentially fragile optical fibers.

In embodiments, the distal end 1008 of the fiber probe can be positioned in an endpiece 1034 such as the ones described with respect to FIGS. 1A-1B, for example. The endpiece can include a handle, lens, and other protective/encasing materials to hold the fibers bundle 180 together and facilitate a user positioning the distal ends 185 in proximity with a sample, and/or the focused light beams at an optimal height relative to the sample.

The external housing 1042 may be made of materials including: metals, high strength plastics, fiberglass, composite materials or any other suitable materials. The external display 106 and control buttons 107 may be integrated into the front surface of the rugged external housing 1042. The external display 106 may be located on the top portion of the front surface of the rugged external housing 1042, with the control buttons 107 located on the bottom portion of the front surface of the rugged external housing 1042. The excitation fiber proximal end 180*a* and fiber optic probe proximal end 180*b* connect to the internal features of the fiber optic system through ports located on a side surface of the rugged external housing 105. While FIG. 1B shows the fiber optic proximal ends 180*a* and 180*b* to be located the right-side surface of the rugged external housing 1042, the fiber optic proximal ends may be located on any side surface of the rugged external housing 1042. The fiber optic proximal ends 180*a* and 180*b* may be joined together at a y-junction opposite the proximal ends, forming the bifurcated fiber optic bundle 180. The bifurcated fiber optic bundle 180 is located between the fiber optic distal end 185 and the fiber optic proximal ends 180*a* and 180*b*. In use, the fiber optic distal end 185 is configured to directly touch the sample 190 or may be in relatively close proximity to the sample 190, for example using an endpiece that spaces the distal end at a desired distance from the sample.

The configuration of FIGS. 1A-1B, for example, allows a simple user interface to operate an instrument for photothermal characterization of a surface in applications with native environments not suited for removal or preparation of the sample surface, or with difficult access points, or for applications where a surface characterization instrument needs to be portable.

Figure 2A:
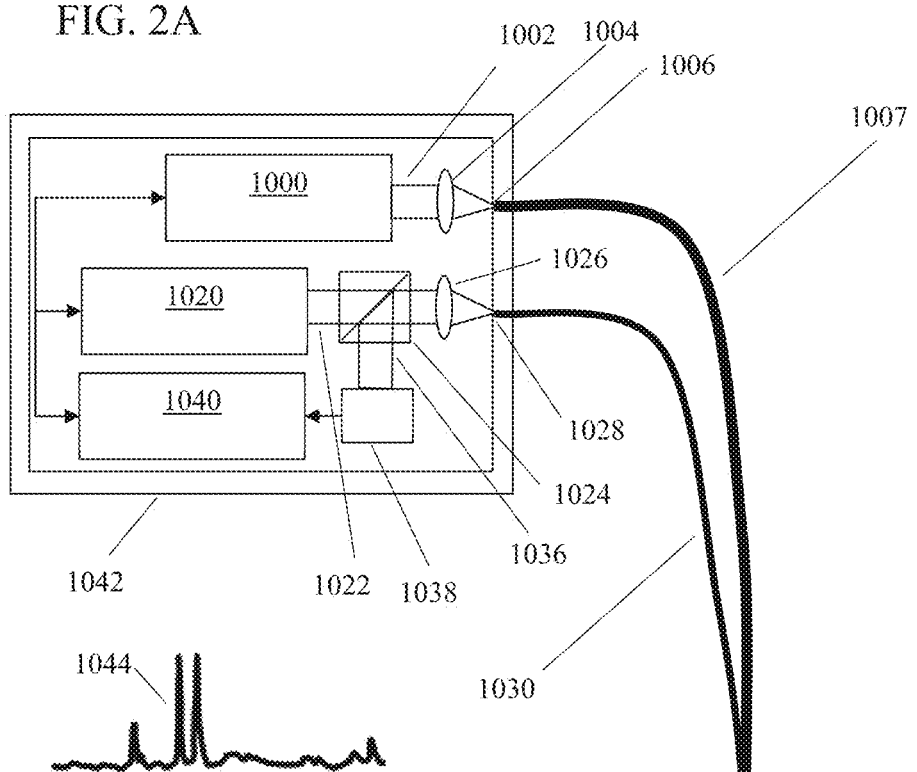
FIG. 2A is a simplified internal block diagram of an alternative embodiment dual beam fiber probe system.

FIG. 2A shows a simplified internal block diagram of an alternative embodiment dual beam fiber probe system. FIG. 2A is based on FIG. 1A and where the same numerical callouts are used, the discussion associated with FIG. 1A applies as appropriate. FIG. 2A is slightly simpler than FIG. 1A as FIG. 2A omits the Raman spectrometer, showing an IR-only configuration that can be made even more compact than the embodiment of FIG. 1A. The embodiment of FIG. 2A employs a bifurcated fiber probe, i.e. a probe where two input fibers are combined into a single integrated fiber probe at the distal end 2000 of the fiber probe. Note that the bifurcated probe embodiment could also be used associated with the FIG. 1A configuration including the Raman spectrometer.

Figure 2B:
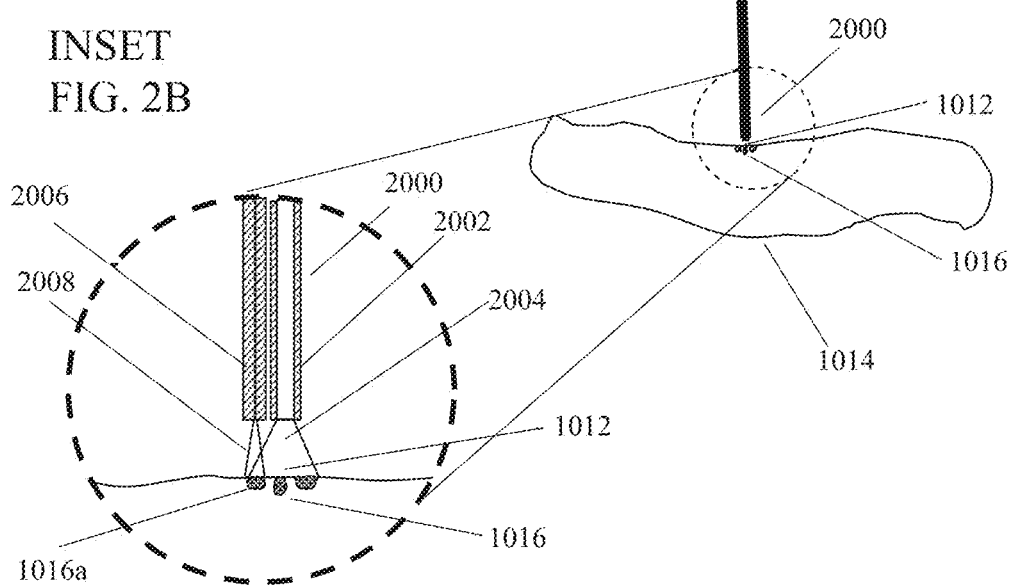
FIG. 2B shows an enlarged view of the encircled region of FIG. 2A.

FIG. 2B shows an enlarged view of the encircled region of FIG. 2A. In the enlarged view the distal end 2000 is shown to comprise at least two fibers arranged in close lateral proximity and with their end faces at a similar height. Fiber 2002 comprises an IR transmissive fiber, for example a chalcogenide, polycrystalline/silver halide or hollow core fiber as described previously. A beam of IR excitation radiation 2004 is emitted from the face of fiber 2002, illuminating a region 1012 of sample 1014. IR absorbing regions 1016 of IR illuminated region 1012 will absorb a portion of incident IR beam 2004 causing local heating of regions 1016. This local heating will be probed by the probe beam as described below. Adjacent to IR fiber 2002 is a second fiber 2006 that is selected to be transmissive for the wavelength of the probe radiation. A beam 2008 of probe radiation is emitted from the end face of fiber 2006, at least partially overlapping IR beam 2004. If there is IR absorbing material within the field of view of probe beam 2008, for example particle 1016*a*, this material will absorb IR radiation, heat up and cause a photothermal distortion in the probe light reflected and/or scattered from the sample. Specifically, the local sample heating may cause a change in the size, shape, deformation, thermal expansion, and/or index of refraction of the IR absorbing region of the sample. This can result in a change in the surface position, curvature, and/or reflectivity, any of which can change the intensity and/or distribution of probe light returning from the sample. At least a portion of the light returning from the sample can be recollected by the probe fiber (or alternately by one or more collection fibers, not shown). The collected probe light can be returned to a detector and analyzed as described associated with FIGS. 1A/1B. The probe beam can be much smaller than the IR beam for several reasons, even without additional focusing optics. First, the core diameter of IR transmissive fibers are 10× or more larger than the core diameters of single mode visible fibers. Second, the numerical aperture of IR transmissive fibers may be much larger than visible fibers. For example, a typical single mode fiber for 532 nm has an NA of around 0.12, whereas a chalcogenide IR fiber can have an NA of 0.28-0.76. Thus, the IR light beam both starts larger and spreads faster than the visible probe beam.

The distal end 2000 of the fiber probe of FIG. 2B may alternately comprise a single fiber that merges the input of fiber 1007 and 1030 into a single fiber, for example using a 1×2 fused fiber optic coupler. For example, the zirconium fluoride and indium fluoride fiber mentioned previously can transmit both probe and IR wavelengths. A wavelength division multiplexer (WDM) can also be used to mix the IR and probe beam wavelengths onto the same output fiber and then re-separate the return probe beam to the detector.

Figure 3A:
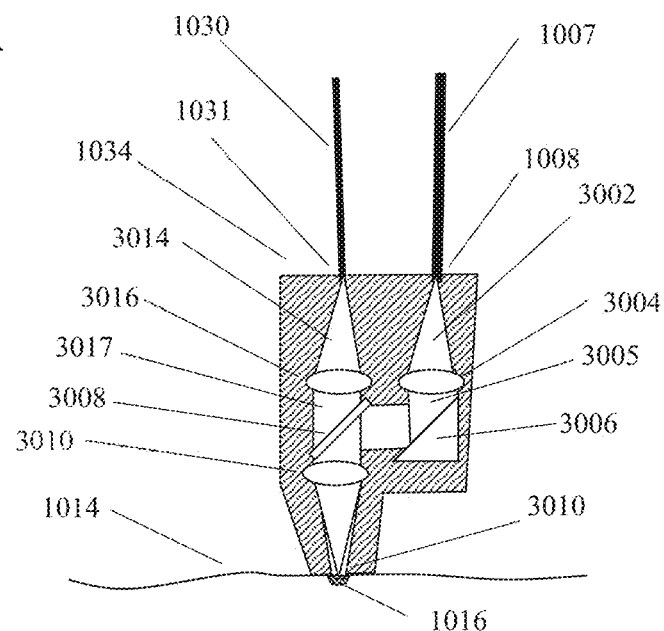
FIGS. 3A-3C are simplified schematic diagrams of embodiments of the distal and proximal ends of a fiber optic probe including capability to perform measurements of heating beam absorption spectroscopy.
Figure 3B:
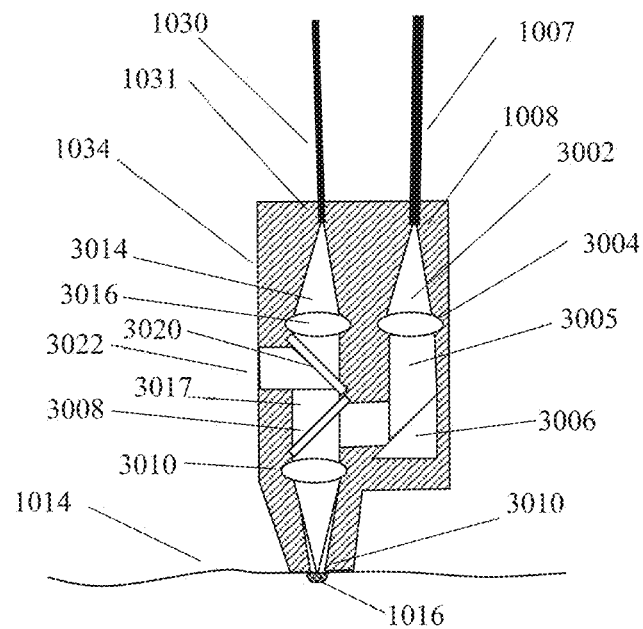
Figure 3C:
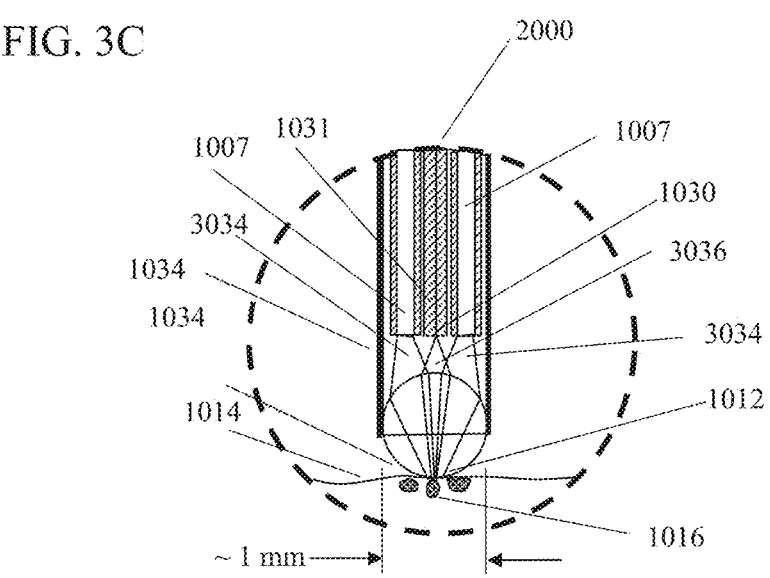

FIGS. 3A-3C show alternative embodiments of the end piece 1034 of FIGS. 1A-1B and 2A-2B. The previous discussion associated with FIGS. 1A-1B and 2A-2B applies as appropriate with respect to common components having common and/or similar reference numerals. FIG. 3A shows end piece 1034 at the distal end 2000 of the fiber probe. IR beam 3002 is emitted from the distal end of IR fiber 1007 which impinges on collimating optic 3004. Collimating optic may comprise one or more lenses, curved mirrors or a combination thereof, etc. as described previously for focusing optics. A substantially collimated beam 3005 is emitted from collimated optic 3005. The collimated IR beam 3005 is optionally directed off one or more turning mirrors 3006 and then directed to a dichroic optic 3008. In the configuration shown, dichroic optic reflects at least a portion of collimated IR beam 3005 towards final focusing optic 3010. This focusing optic may comprise one or more lenses, curved mirrors or a combination thereof. Final focusing optic 3010 focuses the IR beam to a spot 3010 on sample 1014. IR absorbing regions of sample 1014 will absorb at least a portion of the focused IR beam, leading to a localized hot spot 1016. In this dual beam/dual fiber configuration, the probe beam 3014 is emitted from the distal end of probe beam fiber 1030. Probe beam 3014 passes to collimating optic 3016 (also one or more lenses or curved mirrors), resulting in collimated probe beam 3017. Collimated probe beam 3017 in this configuration passes through dichroic 3008 and is also focused onto the sample 1014 by lens 1014. The focused probe beam is then used to detect local changes in the sample temperature due to absorption of IR radiation by the sample as described above associated with FIGS. 1A-1B.

Focusing optic 3010 may comprise entirely reflective optics, e.g. an off-axis parabolic mirror. This arrangement can be advantageous since the reflective optic will have the same focal length for both IR and probe beam, despite the difference in wavelength. In the case that final focusing optic 3010 comprises one or more lenses, the lens(es) may be chosen to be a material that transmits both IR and visible light, for example zinc sulfide, calcium fluoride, barium fluoride, diamond, or for certain probe beam wavelengths, zinc selenide. Other materials that have sufficient transmission for wavelengths of interest for IR and probe beam may also be used. In the case that final focusing optic 3010 comprises one or more lenses, it may be desirable to compensate for refractive index differences between the IR and probe beam wavelengths. For example, it may be desirable to slightly decollimate one or both of the IR beam and the probe beam to arrange the focused spot of both the IR and probe beams at roughly the same focal distance from the focusing optic 3010. Or more specifically, such that the IR and probe beams are focused at the same height/depth on the sample 1014. Creating this parfocality between IR and probe beams can also be arranged by inserting one or more compensation optics (not shown) in either the IR or probe beam path. The compensation optic can provide a correction for the dispersion (e.g. wavelength dependent index of refraction) in the final focus optic 3010.

It should be noted that in various embodiments, some or all of the optics shown in FIGS. 3A-3C can readily be miniaturized. For example, the lenses can be miniature or even microscopic lenses, similar to those used in cell phones, computer hard disks, and microlens applications. Suitable suppliers include Sunex, Framos, Hyperion Optics, and others. Hyperion Optics, for example, manufactures both miniature lenses and mid-IR lenses. Such lenses are available with focal lengths as short as 2 mm or less. Tower Optical manufactures miniature coated prisms down to 0.5 mm across that can be used as turning mirror 3006. Dichroic 3008 can be readily made almost arbitrarily small by cutting plate dichroics to the desired side. As a result, the end piece of FIGS. 1A-1B or FIGS. 3A-3C can readily be made as small 5 mm or less across.

The configuration shown in FIG. 3A shows a dichroic 3008 that reflects IR light and transmits probe light. The inverse configuration can also be used, for example, where the dichroic transmits IR light and reflects visible light. In this embodiment, the location of fibers 1007 and 1030 would be reversed from that shown in FIG. 3A. Suitable dichroics are available, for example, from ISP Optics.

FIG. 3B shows an alternative embodiment to the end piece of FIG. 3A that includes an optical viewing channel FIGS. 3B-3C are based on FIG. 3A and where identical numerical callouts are used, the discussion associated with FIG. 3A applies as appropriate. FIG. 3B includes an additional dichroic 3020 placed in the collimated space of collimated probe beam 3017. Dichroic 3020 can take incoming illumination light and reflect it via focusing optic 3012 to illuminate a region of sample 1014 including the probe beam measuring area, i.e. the location of the focus of the probe beam. Both incoming illumination light and reflected/scattered imaging light can pass through viewing channel 3022. Light passing through this viewing channel can be directed out to a camera-based or visual viewing system to help localize a region on a sample for measurement. For example, an additional port on end piece 1034 can incorporate an input for an optical fiber-based imaging solution, e.g. based on image preserving fiber arrays as used in fiber optic endoscopy products. Alternately, a miniature camera/lens system, for example, similar to those used in cell phones can be mounted directly within the end piece 1034 if desired. In the embodiment in which an optical viewing channel is included spectroscopic measurements can be directly correlated with video images obtained. In the configuration shown in FIG. 3B, dichroic 3020 would be selected to reflect the illumination/optical viewing light and transmit the wavelength of the probe beam. Alternately the probe beam input and optical viewing channel can be swapped such that dichroic 3020 would reflect the probe beam and transmit the illumination beam. The viewing channel and dichroic could alternately be inserted into the IR beam path instead. Suitable dichroics for probe beam/viewing beam separation are available, for example, from Semrock and Chroma and other vendors.

FIG. 3C shows a close-up view of alternative embodiment of endpiece 1034 employing a plurality of excitation and collection fibers. The distal end 2000 of the fiber probe comprises the distal ends of one or more IR fibers 1007 (two shown in this example) and one or more probe fibers 1030 (one shown in this example). In the configuration shown, endpiece 1034 can be a low-profile protective sheath, for example, a stainless steel tube. IR light 3034 emitted from the distal end(s) of IR fiber(s) 1007 is focused onto a region 1012 of the sample using a focusing optic 3032, in this case a ball lens. Probe light 3036 is emitted from probe fiber 1008 and optionally focused by focusing optic, for example, the same focusing optic 3032 that focuses the IR light. To optimize the spatial resolution in various embodiments, the positioning of the fibers, ball lens and sample can be optimized to minimize the size of the visible probe beam spot and, if necessary, at the expense of the size of the IR beam. In many applications, available IR sources provide an excess of power to the sample so that accepting a larger spot size may not degrade the measurement. Suitable ball lenses can be made from material that is sufficiently transmissive at desired IR and probe wavelengths, for example zinc sulfide, zinc selenide, calcium fluoride, barium fluoride, sapphire, diamond and other materials. Suitable ball lenses with broad mid-IR transparency are available for example from VY Optoelectronics Co. Changchun Sunday Optoelectronics, Changchun Realpoo Photoelectric Co. Conventional sapphire ball lenses available from many suppliers can be suitable for shorter wavelengths, for example out to ~5 um or more, depending on the diameter of the ball lens.

The configuration of FIG. 3C is compatible designs requiring extreme miniaturization, e.g. endoscopic applications. For example, ball lenses with wide IR transmission made of ZnSe or ZnS are available in diameters down to the scale of 1 mm, providing an extremely compact endpiece solution to fit within a very small footprint. Sapphire ball lenses are available even smaller, for example down to 0.30 mm in diameter from Edmund optics, still providing acceptable IR transmission for a significant fraction of mid-IR wavelengths. Multiple IR and/or probe fibers can be accommodated in a small footprint as well. For example, silver halide IR fiber is available from IR flex with a cladding diameter of 0.170 mm and single mode optical fiber for visible light is available for Thorlabs with a cladding diameter of 0.125 mm. In embodiments, at least one IR fiber and one probe fiber and a sapphire ball lens may be arranged within an overall fiber probe diameter as small as 0.3 mm. Using more IR and/or probe fibers, larger diameter fibers and larger ball lenses, it is still possible to create a fiber probe with an end diameter of less than 0.5 mm, less than 1 mm or less than 2 mm.

Figure 4:
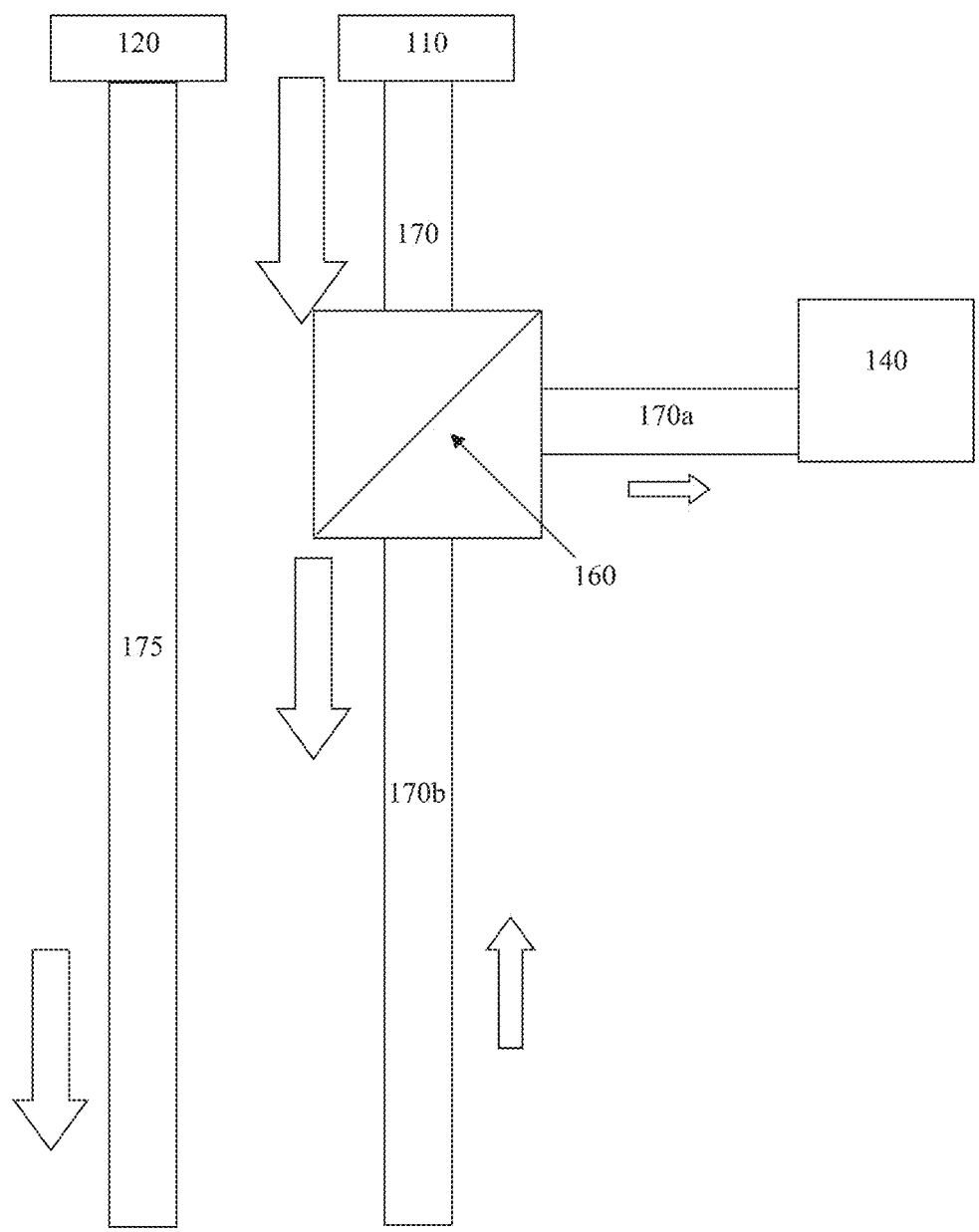
FIG. 4 shows the path of light and relative light intensity through the dual beam probe system.

FIG. 4 shows the path of light and relative light intensity through the apparatus 100. The emitted pump beam 175 travels from the pump beam source 120 and toward the fiber optic proximal end 180a (not pictured). The sensing beam source 110 emits an incident probe beam 170 toward an optical beam splitter 160. Probe beam 170b passing through the beam splitter 160 is directed toward the fiber optic proximal end 180b (not pictured) and is of lower intensity than the incident probe beam 170. Probe beam 170b is transmitted through the fiber optic bifurcated bundle 180, interacts with the sample, and is transmitted through the fiber optic bifurcated bundle from the distal end 185 to the fiber optic proximal end 180b. The probe beam 170b that is collected by the bifurcated fiber optic bundle is of lower intensity than the probe beam 170b prior to transmission through the bifurcated fiber optic bundle. The probe beam 170b is reflected off the beam splitter 160 and the received probe beam 170a, which is lower in intensity than the collected probe beam 170b, is transmitted to the detector 140.

Figure 5A:
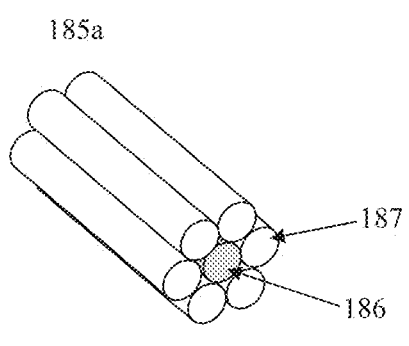
FIGS. 5A-5C are exemplary depictions of showing the terminal surfaces of the fiber optic distal end in various configurations.
Figure 5B:
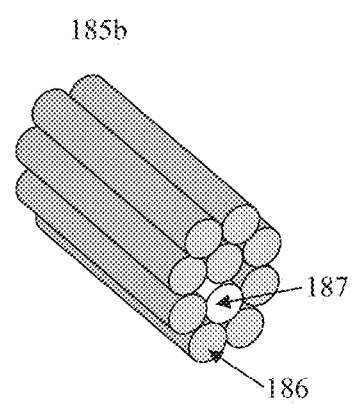
Figure 5C:
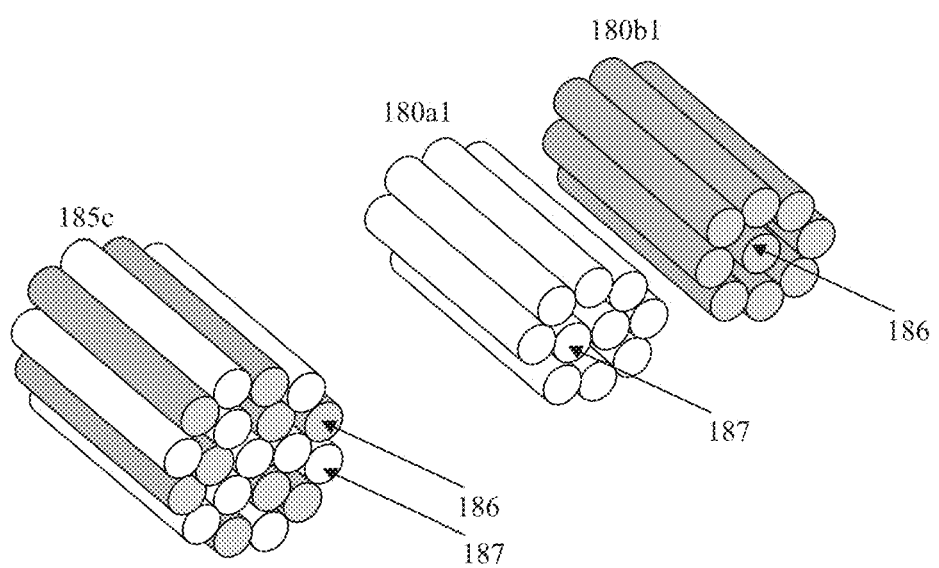

FIG. 5A-FIG. 5C show diagrams of the terminal surface of the fiber optic distal end 185. In one embodiment, FIG. 5A shows a radial configuration with a central optical probe radiation compatible fiber 186, surrounded with a plurality of IR radiation compatible fibers 187. In some embodiments, additional rows of IR radiation compatible fibers 187 or probe radiation compatible fibers 186 may be arranged, extending outwardly from the central optical fiber. FIG. 5B shows a linear configuration of the terminal surface of the fiber optic distal end 185, with one each of a central optical UV probe radiation compatible fiber 186 and central optical IR radiation compatible fiber 187. The central fibers are surrounded by IR radiation compatible fibers 187, arranged to be radially extending from the central optical fibers. FIG. 5C show the distal and proximal ends of a 19 to y-bundle bifurcated fiber optic bundle, arranged with a matrix configuration on the distal end 185c and proximal ends of IR radiation compatible bundles 180a1 and probe compatible bundles 180b1. In each embodiment, the IR radiation compatible fiber 187 and probe radiation compatible fiber 186 are coated with a cladding 188, comprised of a low refractive index material.

For each of the embodiments of FIG. 5A-FIG. 5C, the distal and proximal ends of the fiber optic probe are connected by the bifurcated bundle 180. The fiber optic bifurcated bundle 180 may be made of materials including polycrystalline/silver halide materials, chalcogenide materials, silica, glass, and organic polymers. The various embodiments are selected with different configurations because the intensity of returned light for each fiber differs based on the angle of reflection of the probe beam; by clustering and combining different fiber types, it is possible to maximize the return of light to the detector.

Spatial Resolution

In various embodiments, the spatial resolution that can be achieved can be set by one or more of (1) the size of the probe beam; (2) the area of overlap of the pump and probe beams; (3) the frequency of modulation of the pump beam. When the modulation frequency of the IR beam is high enough such that the thermal diffusion length is much smaller than the spot size of the probe beam, then the spatial resolution can be much smaller than the IR beam spot size. The Abbe spatial resolution limit R is defined as $\lambda/2NA$ as described above, assuming a perfect Gaussian beam and no aberrations in the focusing optics. For example, using a 405 nm wavelength probe beam to read out the IR absorption using an NA of 0.78, this leads to an achievable spatial resolution with the probe beam of 260 nm. By comparison, the same diffraction limit at a wavelength of 10 μm in the mid-IR would give a diffraction limited resolution of 6.4 μm, almost 25× coarser. As such the IR absorption profile of the sample can be probed on much smaller length scales than the spatial resolution limit that would otherwise be constrained by the focus spot size of the IR beam. Even better spatial resolution can be achieved for example by using ultraviolet radiation for the probe beam. In practice, it is possible to achieve spatial resolution of less than 1000 nm, less than 500 nm, and less than 200 nm, in embodiments. Using schemes to control the overlap of the IR and probe beams to less than the diameter of the probe beam can be used to achieve spatial resolution better than the diffraction limit of the probe beam, for example less than 100 nm.

Figure 6:
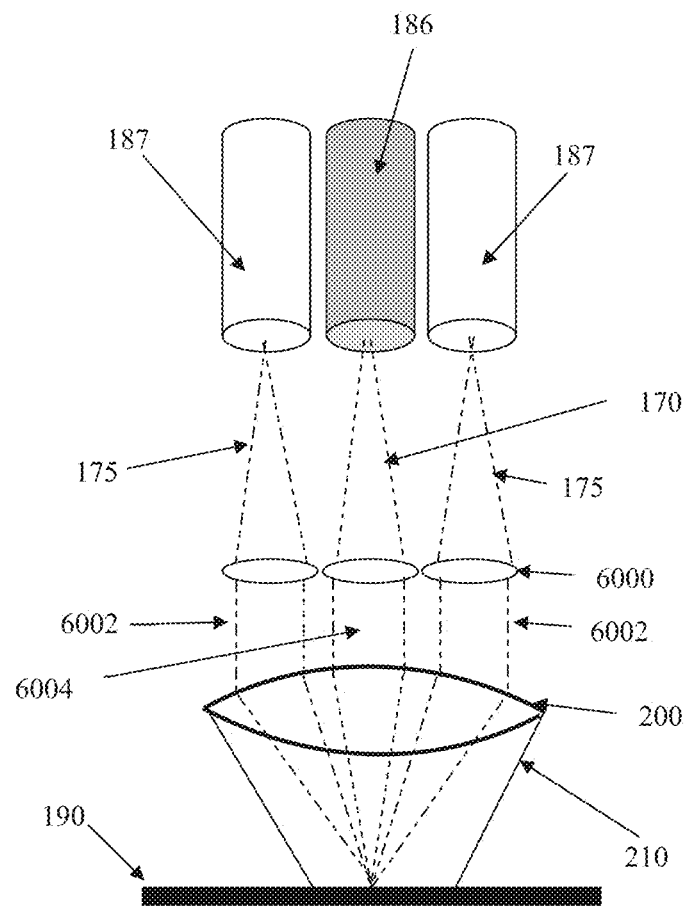
FIG. 6 is a simplified schematic diagram of an embodiment including an optional micro lens array, a focusing lens and contact prism for focusing a probe light source and an IR excitation light source on a specific location within a sample.

FIG. 6 is a simplified schematic diagram of an embodiment including an optional micro lens array, a focusing lens and contact prism for focusing a probe light source and an IR excitation light source on a specific location within a sample. IR radiation 175 is emitted from the distal ends 187 of one of more IR compatible optical fibers. Probe radiation 170 is emitted from the distal ends 186 of one or more probe radiation compatible fibers. Both the IR beam(s) 170 and the probe beam(s) 175 are transmitted to one or more collimating optics 6000 to produce roughly collimated IR beam(s) 6002 and probe beam(s) 6004. Collimating optics 6000 may be one or more lenses, curved mirrors or a collection thereof. In one embodiment, collimating optics 6000 may comprise microlenses or a microlens array. Collimated IR beam(s) 6002 and probe beam(s) 6004 are then focused using focusing optic 200 to locations on sample 190 where the foci of the IR and probe beams are at least partially overlapping. Focusing optic 200 may comprise on or more lenses, curved mirrors or a combination thereof. Focusing optic 200 may also further comprise a contact prism 210 to ensure that a sample 190 in contact with the bottom of contact prism 210 is at the optimal focus of focusing optic 200, i.e. that the position of the sample 190 is at an optimal distance from the focusing optic to create optimal focused spot size for at least one of the IR and probe beam. In some embodiments, the contact prism may comprise a solid exterior structure that contacts a sample or sample substrate along the periphery, while the interior of the prism is filled with a liquid, a gel, a solid, a gas, and/or a vacuum. In other embodiments the contact prism comprises a solid transparent material, for example, glass, quartz, zinc sulfide, zinc selenide, calcium fluoride, barium fluoride, diamond, and/or other materials with sufficient optical transmission for the selected wavelengths of the IR and probe beams. In other embodiments, the contact prism may include a layer of ambient air or noble gas between the surface proximate to the sample and the sample surface. Light may be reflected or scattered off the sample 190 and transmitted through the contact prism 210, focusing optic 200, and up at least one optical fiber back to the one or more detector as described associated with FIG. 1A.

In alternate embodiments, the fiber optic distal end 185 is placed in direct contact with the sample 190 or is placed at a distance from the sample 190, and without the microlens 200 or contact prism 210.

In another embodiment, the fiber optic distal end 185 has features to facilitate x- or y-positioning and identification of position on the sample 190. For example, the fiber optic distal end 185 may be positioned by a surgical robot or other mechanical device (not shown) that monitors and records the location of the fiber optic distal end 185 with respect to the position of the sample 190, at all times. In another embodiment, the fiber optic distal end 185 is manually controlled by a user with triangulation sensors, or other tracking features, that record the real-time location of the fiber optic distal end 185 in space. The fiber probe can also be incorporated into a rigid borescope to analyze hard to reach/hazardous areas. The fiber probe can also be incorporated into and/or a flexible endoscope. In particular, the fiber probe can be incorporated into surgical endoscopes for in vivo spectroscopic analysis, for example, for real-time biopsy analysis and/or to help guide a surgeon to analyze and remove diseased tissue in real time. This is a particularly advantageous embodiment as the current fiber probe can have a minimal impact on the size of an endoscopic probe. Surgical endoscopes can already have channels for illumination, optical viewing, gas, suction, irrigation, and other surgical functions. Because the dual beam fiber probe measurement can be performed with as few as 1-2 fibers with external diameters as small as 125-170 μm, these fibers can readily be integrated into an endoscope without substantially affecting the diameter of the probe end of the endoscope.

In another embodiment, where a bundle of fibers are used that collect light dependent upon the angle of reflection, an additional lens may be used to focus the beam to a post before the detector, and a pinhole may be placed at the focused spot to block light that is scattered or reflected from regions outside the sample focal plane. Probe light detector 140 can be a detector that measures the relative intensity of the beam incident on it, for example a conventional photodiode, an avalanche photodiode, photomultiplier tube, and/or other detector that produces a signal that a signal indicative of an intensity of the light incident on the detector. Alternately, the detector 308 can be a position sensitive detector, for example a linear photodiode, a dual or quad segment detector or a multi-detector array. In this embodiment, the detector can also be sensitive to positional shifts in the reflected/scattered beam, for example due to angular deviations in the beam and/or lateral shifts. Alternately detector 140 may comprise a phase sensitive detector, comprising further an interferometric detection scheme that produces a signal indicative of the optical phase or optical phase shift of the beam incident on the detector. In these embodiments, the system can measure the change in intensity, beam angle and/or optical retardation induced by a temperature change in the sample due to the interaction or absorption of infrared light by the sample. Detector 140 may also be an array detector and/or a camera that is sensitive to light at the probe wavelength.

The receiver can comprise a camera and/or an array detector. The use of a camera and/or array detector can provide a substantial improvement in measurement throughput by enabling parallel measurements of multiple locations on the sample simultaneously. To achieve high spatial resolution, it may be desirable to use a camera or array detector that has a fast response time, or equivalently a high measurement bandwidth. A reason for this is that as pump radiation or another a secondary pump radiation is absorbed by the sample, the heat generated by the absorbed light can diffuse away from the absorbing region, causing a reduction in the spatial resolution. To maintain high spatial resolution, it can be desirable to employ IR laser sources with high repetition rates and detectors with high bandwidths that enable measurements off the probe light on time scales shorter than the thermal diffusion time for a desired spatial resolution.

Figure 7A:
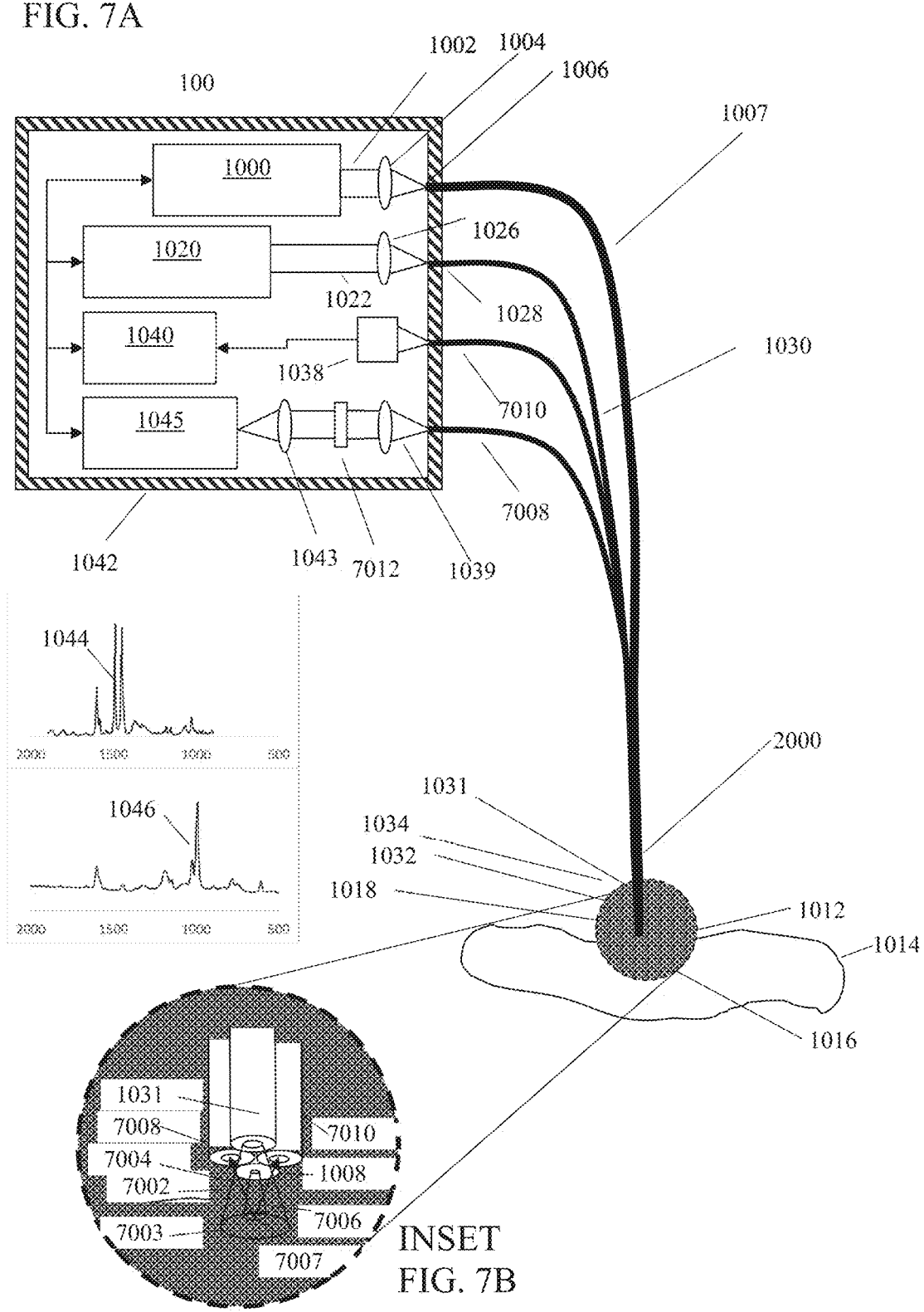
FIG. 7A is a simplified internal block diagram of an alternative embodiment dual beam fiber probe system using a multiply bifurcated fiber probe.

FIGS. 7A-7B illustrate an alternate embodiment of the dual beam fiber probe using a multiply bifurcated fiber probe. FIG. 7A is based on FIGS. 1-2 and where identical numerical callouts are used, the discussion associated with FIGS. 1-2 applies as appropriate. As discussed before, IR source 1000 emits a beam of IR radiation that is coupled into optical fiber 1007 and probe radiation source 1020 emits a beam of probe radiation that is coupled into fiber 1030. As shown in INSET FIG. 7B, a beam of IR radiation 7002 is emitted from the distal end 1031 of IR fiber 1030, illuminating a region 7003 of sample 1014. A beam of probe radiation 7006 is emitted from the distal end 1008 of probe fiber 1007 illuminating a region 7007 of the sample at least partially overlapping the IR illuminated area. Radiation that is reflected and/or scattered from the probe illuminated region of the sample (indicated by arrows 7004) is collected at the distal ends of one or more collection fibers 7008 and 7010. Collected probe radiation is transmitted up the collection fibers back into enclosure 1042 (or alternately into a separate enclosure). At least a portion of collected probe light is re-emitted from the proximal end of fiber 7010 where it is coupled to detector 1038, optionally incorporating additional focusing optics (not shown).

As discussed before, signals from detector 1038 are analyzed to detect changes in collected probe light as a function of IR absorption by the sample, thus providing a signal indicative of IR radiation by the sample. A separate fiber 7008 can optionally be used to collect and transmit Raman scattered light and transmit the Raman scattered light to Raman spectrometer 1045, to produce a signal indicative of a Raman spectrum of the probe illuminated region of the sample. One or more Raman edge filters 7012 can be inserted in the beam path to block the probe excitation wavelength and only transmit wavelength shifted probe light. The Raman edge filter(s) can be in the enclosure 1042, inside the Raman spectrometer 1045, at either the proximal or distal end of fiber 7008 or any combination thereof. The arrangement of FIG. 7A has several advantages. First, it eliminates the beam splitter 1024 of FIG. 1A and any associated losses. It also allows separate optimization of the probe beam fibers for the illumination beam 7006 vs the reflected/scattered radiation. For example, probe illumination fiber 1008 can be a single mode fiber to provide a small illumination area 7007 on sample 1014 whereas the collection fibers 7008 and 7010 can be larger diameter (and/or larger NA) for more efficient collection of reflected/scattered light.

Figure 8:
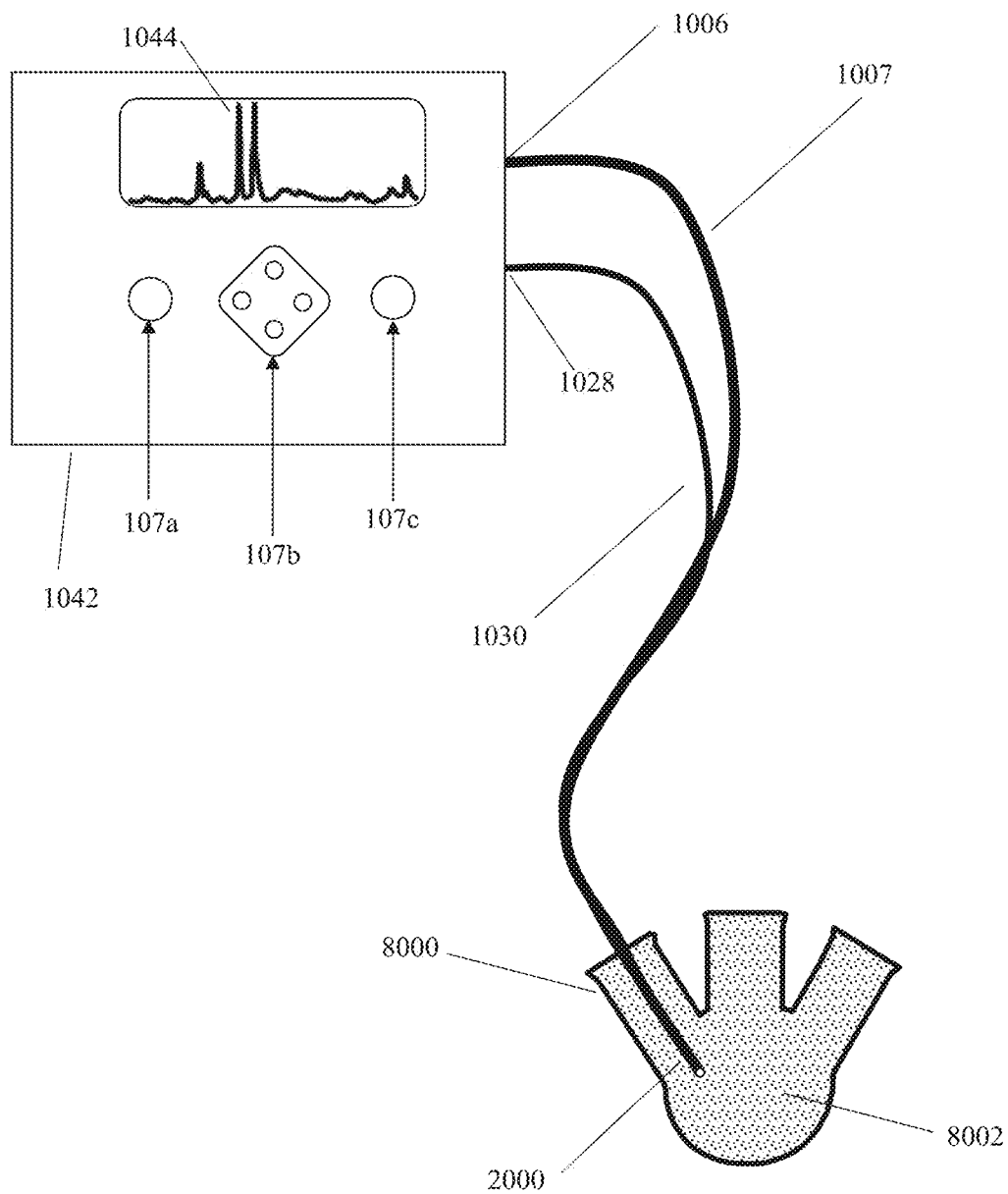
FIG. 8 shows a conceptual simplified external block diagram of the fiber optic probe system of the embodiment of FIG. 1B used for reaction monitoring in a reaction chamber.

FIG. 8 illustrates the use of the dual beam fiber probe for reaction monitoring in a reaction chamber. FIG. 8 is based on FIG. 1B and, where identical numerical callouts are used, the discussion associated with FIG. 1B applies as appropriate. In FIG. 8, the distal end 2000 of the fiber probe is inserted into a reaction chamber 8000 to monitor reaction products over time using at least one of infrared spectroscopy, Raman spectroscopy and fluorescence. Reaction chamber 8000 may be filled with one or more fluids 8002 such that the distal end 2000 of the fiber probe is immersed in the fluid. The dual beam fiber probe can then capture IR spectra, Raman spectra, and/or fluorescence measurements and display the resulting spectra 1044 on the user interface display of the unit. The fiber probe controller can also be programmed to analyze spectra to monitor the concentrations of any desired (or undesired) reaction products and send reaction status messages, issue alarms, initiate or terminate process steps, etc. based on the spectroscopic readings of the fiber probe. The reaction vessel 8000 illustrated is a laboratory scale reaction vessel, but the fiber probe could also be installed in an industrial scale process reactor.

Figure 9:
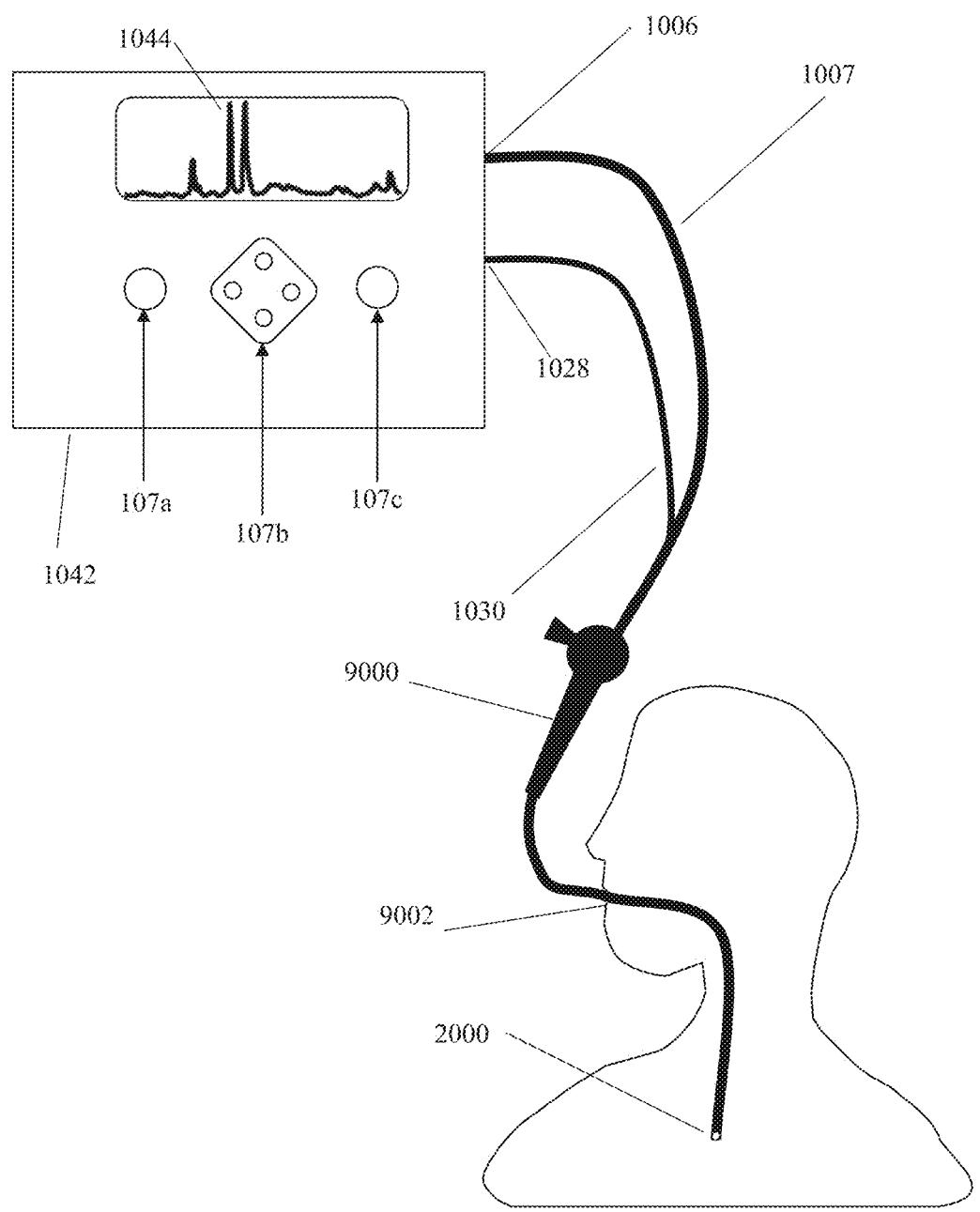
FIG. 9 shows a conceptual simplified external block diagram of the fiber optic probe system of the embodiment of FIG. 1B used for in vivo spectroscopic analysis.

FIG. 9 illustrates using the dual beam fiber probe for in vivo spectroscopic analysis. FIG. 9 is based on FIG. 1B and where identical numerical callouts are used the discussion associated with FIG. 1B applies as appropriate. FIG. 9 shows an embodiment where the dual beam fiber probe is integrated into an endoscopic instrument 9000 suitable for in vivo investigation of tissue, for example, inside an animal or a human subject or patient. The dual beam fiber probe can be inserted into the body through an orifice 9002 and/or through a surgical incision. The distal end 2000 can be steered to one or more tissues of interest in the same manner as conventional fiber endoscopes, for example using integrating viewing optics and remote steering of the probe end 2000. When the fiber probe is positioned as desired, the IR and probe beam illumination can be enabled and IR and/or Raman spectra and/or fluorescence data can be collected from the tissue in the vicinity of the distal end 2000 of the fiber probe. The collected spectra can be compared against reference spectra and/or analyzed against reference models for tasks including tissue identification and classification, in vivo cancer biopsy, identification of diseased or necrotic tissue, identification of pathogens, presence of infections, and other diagnostic tasks. The dual beam fiber probe as used in various embodiment has a significant advantage over all other fiber-based probes for these types of applications because of reasons mentioned previously: (1) correlative capabilities of simultaneous IR/Raman/Fluorescence; and (2) elimination of size, shape, and wavelength dependent spectral artifacts in the IR spectra.

Figure 10:
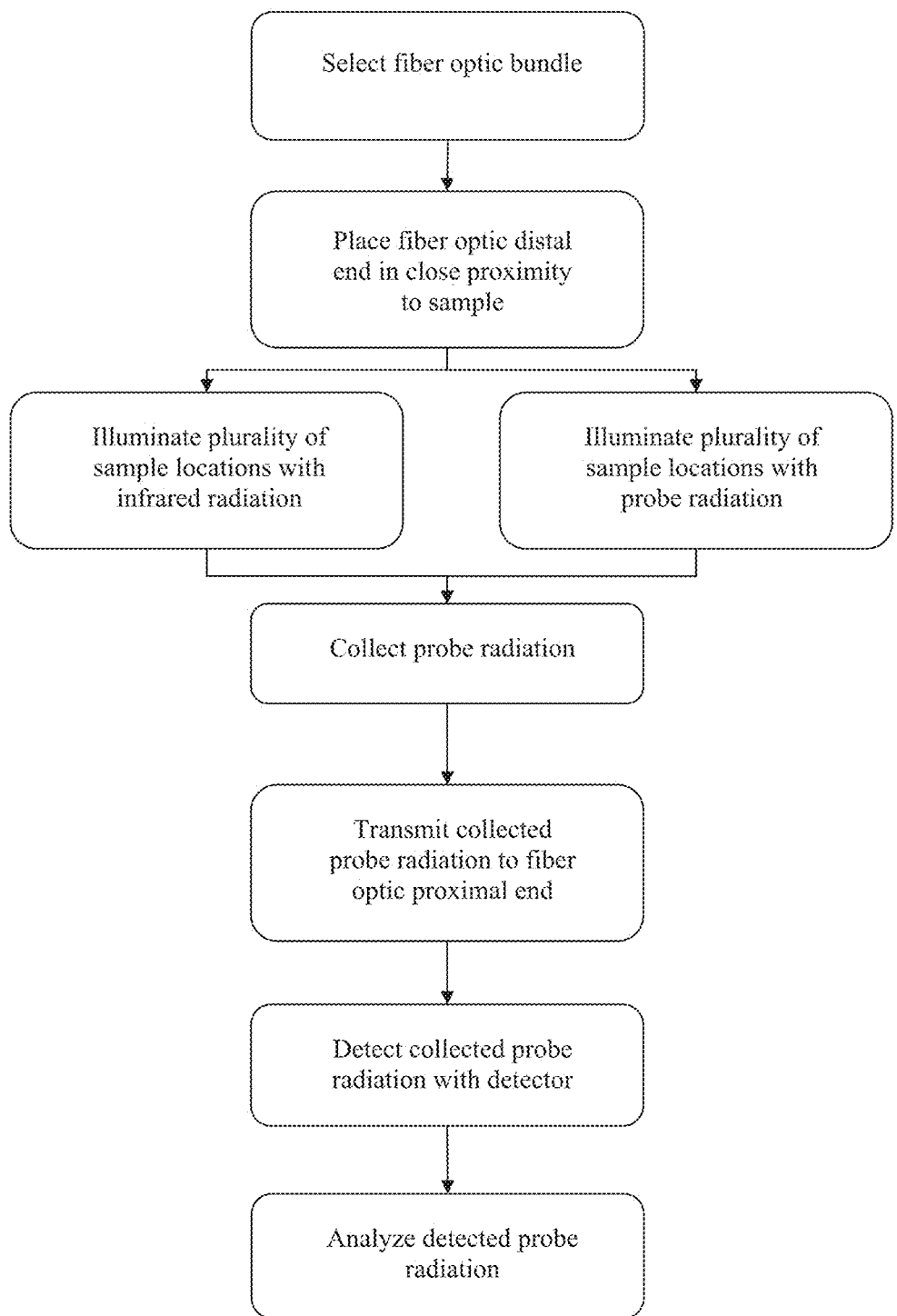
FIG. 10 is a flow chart of the method of using the fiber optic embodiments.

FIG. 10 describes a method of using the various embodiments of a dual beam photothermal spectroscopy system as described. The operator selects a fiber optic bundle for the correct apparatus configuration, sample matrix, source of pump radiation, and source of probe radiation. The operator then places the fiber optic distal end of the fiber optic bundle in close proximity to, or touching, a sample. The operator may then use a user interface (e.g. FIG. 1B) to control the apparatus, and the apparatus illuminates a plurality of locations of the sample with a source of pump radiation transmitted from a fiber optic proximal end to a fiber optic distal end to create a pump illuminated spot on the sample. The operator then uses a user interface and control buttons (e.g. FIG. 1B) to control the apparatus, and the apparatus illuminates a plurality of locations of the sample with a source of probe radiation transmitted from the fiber optic proximal end to the fiber optic distal end of the fiber optic bundle. The probe radiation is collected form a plurality of sample locations and is transmitted from the plurality of sample locations from the fiber optic proximal end of the fiber optic bundle and is then detected with at least one detector. In the final step, sensor detected probe radiation is analyzed to generate signals indicative of infrared absorption of the plurality of locations on the sample, where the signals indicative of infrared absorption of the plurality of sample locations achieve a spatial resolution of less than 1 micrometer.

The apparatus can also include additional interferometers, filters, detectors, and spectrometers to enable simultaneous or sequential Raman spectroscopy and/or fluorescence measurements. In these embodiments, one or more optional fluorescence and/or Raman filters can be installed to substantially block light at the probe light source center wavelength and pass light that is wavelength shifted from the probe wavelength. This approach allows detection of inelastically scattered light, including but not limited to Raman and fluorescently shifted light. Additional optional detectors can be used to detect and/or spectrally analyze the wavelength shifted light. Specifically, a Raman spectrometer can be used to measure Raman spectra from light that emanates from the tip-sample region due to the excitation by the probe light beam. The receiver module can be free space coupled and/or can have one or more elements that are fiber coupled. For example, the collected probe light may be coupled into an optical fiber and then transmitted to a fiber coupled Raman spectrometer.

Another advantage of the photothermal IR technique is that it overcomes the limitations of conventional reflection-based IR spectroscopy. In conventional reflection-based IR spectroscopy, the sample is illuminated with IR light the light that is transmitted through the sample or reflected/scattered from the sample is collected and analyzed. Transmission IR absorption spectra are extremely useful for analyzing the chemical makeup of a sample because there are vast databases with bulk transmission spectra for hundreds of thousands of materials. Transmission IR spectroscopy, however, generally requires preparing a thin section of a sample, which can range from time consuming to impractical or impossible, depending on the type of sample.

Alternative IR spectroscopy techniques exist that are based on reflectance arrangements, where the system can measure the IR light that is reflected and/or scattered from the sample. This can eliminate the need to prepare a thinly sectioned sample, but reflection-based IR spectroscopy has many artifacts relative to transmission IR spectroscopy. The artifacts are primarily due to a variety of factors resulting from the scattering of light and dispersive effects resulting from contributions of both the real and imaginary components of the index of refraction in the amount of reflected/scattered IR light. These artifacts frequently distort measured IR spectra versus transmission IR spectra, making chemical analysis and identification significantly more challenging.

The dual beam technique described above produces spectra that are substantially free of dispersive artifacts associated with conventional reflection/back scattered IR spectroscopy. Because the probe beam is sensitive only to the change in temperature of the sample due to the photothermal response (e.g., from change in index of refraction and/or thermal expansion), it is completely independent of the wavelength dependent reflectivity and/or scatter of the IR beam. As such the disclosed techniques provide the ability to provide IR absorption spectra that correlate well to conventional FT-IR spectroscopy, substantially without dispersive artifacts, and allow accurate material characterization and identification. These characterization spectra can include in mid-IR wavelengths where the so-called "fingerprint bands" exist that provide rich information for discriminating materials, even highly similar materials.

It is not strictly necessary for the sensing or probe beam to have a shorter wavelength than the heating beam, in embodiments. While this is desirable for microscopic measurements where the desired spatial resolution is smaller than the optical diffraction limit of the heating beam, it is not needed for wide area measurements with coarser spatial resolution requirements or for bulk measurements. Rather, it can be sufficient in some embodiments to use a substantially fixed wavelength probe beam, rather than necessarily a shorter wavelength. Using a fixed wavelength probe beam allows the measurement of the photothermal distortion of the sample with no issues of wavelength dependent variations in the optical properties of the sample as is the embodiment when measuring an IR response from the heating beam by observing the reflection over the IR wavelengths of the incident beam. This insight allows the application of photothermal IR technique using probe beams that are of any desired wavelength that produces sufficiently high power to produce a detectable signal.

Probe or sensing beams can be produced by sensing beam sources such as lasers operating in the UV spectrum, visible spectrum, near IR spectrum, or even the mid-IR spectrum. It also may not be necessary to employ the same power density for widefield/bulk applications as for a microscope implementation. Although the power density and associated photothermal deformation may be lower when the IR and/or probe beam are spread over a larger area, the aggregate impact on the sample may still be detectable. For example, a detection system that integrates the small photothermal distortion over a large area may have sufficient sensitivity even at small optical power densities. One way of achieving this for example is to use camera 210 or an alternate camera or array detector in received 142. A camera or array detector can measure the small change in intensity and/or position of reflected or scattered light over a plurality of pixels and then coherently sum the aggregate impact on the motion/intensity of scattered probe light collected from a large area. Speckle patterns from rough samples, as discussed previously, can be analyzed to determine a signal that is indicative of the photothermal distortion of the sample and in turn the IR absorption of the sample.

The ability to obtain spectra from a wide area of a sample makes the photothermal IR technique viable for use in a variety of applications, including material inspection, material composition analysis, evaluation of material treatments, hazardous materials detections, detection of defects and contaminants, and process control to name a few. For example, a dual beam IR/Raman system could be used to performing incoming material inspection on bulk materials to verify composition against a vendor or customer specification Similarly, the system can be used to determine the material composition of an unknown material or check the composition against some predetermined targets. In this embodiment, the measured spectra can be a linear superposition of component spectra scaled by their relative concentrations. With chemometric or spectral decomposition techniques, the system can be used to deconvolve the mixed spectra into component spectra and relative concentrations.

The probe beam can be used for multiple purposes. It can be used to probe the IR absorption of the sample due to the photothermal process described previously, but it can also be used to generate Raman scattering and/or fluorescence in the sample. For the IR measurements, as before, regions of the sample that absorb IR light will heat up, resulting in a photothermal distortion of the sample associated with the absorbing regions. The photothermal distortion of the sample is detected via the probe beam whose beam shaper and/or trajectory can be modulated by the photothermal heating of the sample. Probe light returning from the sample (along with any resulting fluorescent and/or Raman scattered light excited by the probe beam) can be collected by optic or alternately a separate offset collection optic (not shown). In the embodiment, the probe light is collected by the same optic, the collected probe beam reflects off beam combiner and into beam splitter where a portion of the beam passes through to receiver. The receiver can comprise any desired combinations of optical sensors and spectrometers. Electronics can be used to amplify/condition and demodulate sensor and/or spectrometer signals to compute signals indicative of IR absorption, Raman scattering and/or fluorescence signals. The entire device may be surrounded with a ruggedized case 105 to permit usage in harsh environments and/or workplaces where the device may be exposed to shocks, drops, and/or chemical exposure.

Similarly, laser diodes suitable for sensing probe light sources are available from many vendors in a size suitable for a handheld device. Thorlabs sells many laser diode devices ranging from a few mW to more than a watt over many wavelength ranges. For example, Thorlabs sells a laser diode part number LD785-SEV400 in a TO-9 can (9 mm diameter) with 400 mW of optical power at 785 nm, sufficient for both sensing beam measurements and as a source for Raman spectroscopy. Alternate packages are available with fiber coupled laser diodes in many wavelengths.

Miniature collimating lenses are also available and complete laser diode modules with collimation and drive electronics are also available in a variety of form factors from various vendors. IR and probe beam diameters can be kept at the size of a few millimeters or less to enable the use of small or miniature optics for beam combiner 904, focusing optic 906, and beam splitter 916. The beam combiner, focusing optic and beam splitter could each be 5 mm or less across, in an embodiment. For example, Edmund Optics makes a polarizing beam splitter in a 5×5×5 mm size and smaller beam splitters and other optics can be fabricated on a custom basis. Visible laser diodes are similarly small, for example less than about 5 mm long and less than about 9 mm diameter. Thermoelectric or other cooling may be desired, but the space required for this can be on the scale of a few mm to a few cm depending on the optical power level and associated heat load. Optical detectors, Raman spectrometers, and/or cameras are also available in miniature form factors with sizes on the scale from a few mm to a few cm. Power supplies, signal conditioning and computational electronics can also be miniaturized, down to the scale of a few cm for the functions required. As such, it is possible to assemble an entire handheld photothermal probe device to fit into a package that is smaller than 125 mm across, in one embodiment.

For higher power applications, it may be desirable to have a portion of the device remoted, for example with power supply, batteries, additional computation resources, and/or larger IR and/or probe light sources. In this embodiment, the handheld unit may be coupled to the remote unit via a wired connection or a wireless connection. A wired connection can include one or more cables and/or optical fibers to provide electrical and/or optical coupling between the handheld unit and the remote portion of the device. For example, separate IR and visible optical fibers may transmit the IR and probe light to a handheld unit where the two beams are combined.

The miniature device can be used for a large number of applications, including but not limited to material inspection, material composition analysis, evaluation of material treatments, hazardous materials detections, detection of defects and contaminants, in situ evaluation of biological samples, and process control. In the embodiment of standoff detection, where the unit is used to perform chemical analysis of a distant object, focusing optic can be replaced with a collimating optic so as to emit collimated IR and probe beams. Then the probe beam can measure the photothermal response and hence IR absorption from a distant object. For standoff detection, it is possible to collect reflected/scattered light with the same collimating optic or alternately a separate optic, even with a standalone collector, for example an optical telescope fitted with an optical detector and/or camera.

Auto-Optimization

In embodiments, it is possible for a fiber optic system to have a very large number of degrees of freedom that can require adjustment or optimization. For example, the pump beam power, the probe beam power, the position of the focusing objective, the position of the collection optic (if used), the relative alignment of the IR and probe beams to the focusing optic and the relative alignment of the IR and probe beam to each other are all parameters that can be adjusted as desired by an operator. If these parameters are not monitored, the desired signal may not be measured or there can be a low signal-to-noise ratio. In embodiments, different techniques are used to automate the selection of useful parameters for use in sample evaluation. Some of these have already been described in part, for example associated with beam steering and IR/probe beam overlap. Some other techniques used for automated optimization are discussed below.

Avoiding Sample Damage

One challenge associated with fiber optic measurements is adjusting the signal strength without damaging the sample. To maximize the signal strength it can be desirable to increase the laser power of the pump beam and/or the probe beam. The limit to which the power can be adjusted depends on the absorptivity of the sample at the IR and probe wavelengths, along with the sample damage threshold. There are several ways to maximize the sensitivity while avoiding sample damage. For example, it is possible to record the signal sensitivity and/or signal-to-noise ratio, while increasing the optical power of at least one of the pump source and the probe beam until either (1) the sensitivity/signal-to-noise ratio reaches a maximum; and/or the (2) damage is observed in the sample. Sample damage can be observed in a number of ways. For example, it is possible to perform a spectroscopic sweep by measuring the signal across a plurality of wavelengths. In the case that damage is caused by IR absorption, the damage will occur first at the strongest absorbing wavelengths. Sample damage can be detected by observing non-linearities and/or discontinuities in the spectra. For example, when some materials reach a sufficiently elevated temperature they can undergo a glass to rubber transition, resulting is a significantly larger thermal expansion coefficient and hence a substantially larger change in the index of refraction with temperature dn/dT.

In practice this can mean that strong absorption peaks can look out of proportion to weaker peaks compared to the same measurements performed with lower IR laser intensity. It is possible to calculate for example the ratio in amplitude between a major peak and a minor peak. If that ratio changes abruptly at elevated IR laser powers, it can indicate that the sample is being damaged at the stronger absorption peaks and that lower laser power should be used.

Other samples may be melted and/or burnt at elevated temperatures resulting from excessive laser power. These effects can also be detected via distortions and/or discontinuities in the fiber optic IR absorption spectra. For example, one can measure a series of spectra at increasing laser power. By plotting the amplitude of one or more absorption peaks as a function of laser power the onset of damage can be indicated with a nonlinear response of signal intensity versus laser power, a drop in response, a discontinuity, and/or an irreversible change in the peak intensities or spectral quality. Detecting the onset of any of these conditions can establish a damage threshold that can be used to constrain the laser power. It is also possible to use a video optical microscope with an image compare algorithm. For example, a series of optical microscope images can be obtained with increasing laser power of either the IR beam or the probe beam power. Each subsequent image can be compared to one or any of the images prior. An image compare algorithm can look for differences between the images that are indicative of potential sample damage. For example, static images of the same locations measured below the damage threshold should have substantially no differences except due to camera noise. So, subtracting two images without intervening damage should show minimal difference. But after even subtle sample damage occurs, the image subtraction will reveal a difference zone associated with thermal changes to the sample. This process can be performed automatically by rapidly taking an image alternating with an exposure of increasing IR and/or probe beam power and damage thresholds can be determined for each wavelength range. It is possible to then use these thresholds to dynamically maximize the signal sensitivity and/or signal-to-noise ratio even as a function of wavelength. For example, it is possible to increase the laser power at weakly absorbing wavelengths and reduce the power at strongly absorbing wavelengths. Alternately, it is possible to dynamically reduce the probe beam power at strongly absorbing wavelengths and vice versa.

It is also possible to infer the sample damage threshold by observing the thermal IR radiation emitted from the sample. As the temperature of a sample increases, it emits an increasing amount of IR radiation and the center wavelength of the emission changes in accordance with Planck's law. From the intensity and/or center wavelength of the emitted IR radiation it is possible to estimate quantitatively the temperature of regions of the sample that are illuminated by the IR and probe beams. The temperature can be compared against known or experimentally determined sample threshold temperatures that cause an unwanted material changes. For example, IR and probe beam intensities can be maintained below material transition temperatures for example associated with glass-to-rubber transitions, melting, decomposition, desorption, etc. The sample IR temperatures from thermal radiation emission can be determined for example with an IR detector, an IR camera, and/or an IR spectrometer to measure the intensity and/or center wavelength of the IR emission. While this IR temperature measurement will in general be performed with diffraction limited spatial resolution, it is still possible to use such measurements to infer the maximum temperature within the illuminated volume.

Surface Tracking

In some embodiments, especially non-contact embodiments, measurements on rough and/or highly curved samples may be a challenge as the signal can dramatically decrease as the sample surface moves out of the plane of focus of the probe beam. To overcome this issue, it is possible to dynamically adjust the focus of the probe beam in response to the sample profile. For example in FIG. 6 to accommodate for non-flat surface profile of sample 190, a measurement is made of the position of the sample surface under the microlens 200 to determine a relative distance $Z_0$ from some reference position within the system. The XY locations may for example be a linear array and/or a regular grid of XY locations and/or a select set of XY locations over specific regions of interest. This sample distance $Z_0$ is measured at a plurality of locations, for example across a linear profile or at an array of X, Y locations on the sample to obtain one or more 1D surface profiles $Z_0(X)$ and/or a 2D surface contour $Z_0(X,Y)$.

After measurements of the relative sample height at a plurality of XY locations, the resulting measurements form a profile or surface that represents the variation in height of the sample. Once the desired number of XY locations are measured to create a sample height profile, this profile can be used to make optimal measurements of the signal. Specifically, the sample is moved to a desired XY location, the focus optic is moved to the height recorded during step and the signal is measured. These steps are repeated for as many XY locations as desired. Then a PTP image can be created from the measurements acquired at the optimal focus positions $Z_0$.

This relative sample distance $Z_0$ can be measured in any number of ways, for example with a distance measuring interferometer, a capacitance sensor, by optical triangulation, by confocal optical microscopy, by a white light interferometer, optical autofocus, or other similar means sensitive to the surface position. The detailed shape of the interferogram will depend on the optical bandwidth of the light source used to illuminate the sample. In general, it is preferable to measure with a shorter wavelength, e.g., the wavelength of a probe beam, for example in the UV or visible wavelength range. For a narrowband source, the interferogram will have a generally sinusoidal shape at it is possible to interpolate the relative position of the sample to a nanometer or better. It is also possible to use a less coherent source, for example an LED or a white light source. By measuring the position of the peak of the interferogram at a plurality of X or XY locations on the sample, it is possible to create a map of the sample height to use to obtain optimal measurements of the IR absorption via the measurement technique.

A related way of finding the surface height is by monitoring the DC intensity of the probe beam as a function of the objective height. For example, the probe beam that is reflected/scattered from the sample is directed towards a receiver that can comprise an optical detector. While the AC component of this signal is analyzed by analyzer, the DC component may also be used to determine the relative position of the surface to substantially maximize the signal While the DC signal has a much broader depth of focus, the centroid of the DC signal curve has substantially the same center as the signal curve. The advantage of using the DC signal is that it is many, many times stronger than the photothermal signal and hence can be measured much faster. In addition, measuring the DC signal requires no knowledge of the sample, whereas to obtain a photothermal signal it is necessary to tune the IR laser to an absorbing wavelength of the region of interest of the sample 190. This can be problematic when the sample is an unknown material as it will not be clear what wavelength should be used to optimize the measurement. So, using the probe DC signal to determine the surface height first removes a degree of freedom and ensures that the photothermal measurement is started at a substantially optimal focus height. And as described above, this process can be repeated at a plurality of locations on the sample to make a map of the surface variation across regions of interest of the sample to enable optimal photothermal measurements at those sample locations.

The embodiments described herein are exemplary. Modifications, rearrangements, substitute processes, alternative elements, etc. may be made to these embodiments and still be encompassed within the teachings set forth herein. One or more of the steps, processes, or methods described herein may be carried out by one or more processing and/or digital devices, suitably programmed.

Depending on the embodiment, certain acts, events, or functions of any of the method steps described herein can be performed in a different sequence, can be added, merged, or left out altogether (e.g., not all described acts or events are necessary for the practice of the algorithm). Moreover, in certain embodiments, acts or events can be performed concurrently, rather than sequentially.

The various illustrative logical blocks, optical and control elements, and method steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim While the above detailed description has shown, described, and pointed out novel features as applied to illustrative embodiments, it will be understood that various omissions, substitutions, and changes in the form and details of the devices or methods illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

The invention claimed is:

1. A system for fiber probe-based spectroscopy analysis of a sample, the system comprising:
   an infrared source configured to generate a beam of infrared radiation;
   a probe source configured to generate a beam of probe radiation;
   a fiber optic probe including at least one optical fiber, wherein the fiber optic probe is configured to:
   receive, at a proximal end of the fiber optic probe, the beam of infrared radiation from the infrared source and deliver the beam of infrared radiation from a distal end of the fiber optic probe to the sample;
   receive, at a proximal end of the fiber optic probe, the beam of probe radiation from the probe source and deliver the beam of probe radiation from the distal end of the fiber optic probe to the sample, such that at least a portion of the beam of infrared radiation and the beam of probe radiation overlap one another on the sample;
   collect, at the distal end of the fiber optic probe, probe radiation that is at least one of reflected or scattered from the sample as a collected probe radiation;
   a detector configured to receive the collected probe radiation and produce a signal indicative of an intensity of the collected probe radiation; and
   an analyzer configured to analyze the signal indicative of an intensity of the collected probe radiation to generate a signal indicative of infrared absorption of the sample, wherein the signal indicative of the infrared absorption of the sample comprises an infrared absorption spectrum.

2. The system of claim 1, wherein the fiber optic probe comprises at least two optical fibers.

3. The system of claim 1, wherein the fiber optic probe comprises at least one optical fiber transmissive to the beam of infrared radiation and at least one optical fiber that is transmissive to the beam of probe radiation.

4. The system of claim 1, wherein the fiber optic probe comprises at least one optical fiber formed of one or more materials from the following list: chalcogenide fiber, polycrystalline/silver halide fiber, zirconium fluoride fiber, indium fluoride fiber, and hollow core fiber.

5. The system of claim 1, wherein the system further comprises at least one focusing optic at the distal end of the fiber optic probe.

6. The system of claim 5, wherein the at least one focusing optic comprises:
   a first focusing optic configured to focus the beam of infrared radiation onto the sample; and
   a second focusing optic configured to focus the beam of probe radiation onto the sample so that the beam of probe radiation at least partially overlaps the focused infrared radiation.

7. The system of claim 5, wherein the at least one focusing optic is configured to collimate and/or focus at least one of the beam of probe radiation and the beam of infrared radiation.

8. The system of claim 5, wherein the focusing optic comprises a ball lens.

9. The system of claim 8, wherein the ball lens is transmissive to infrared radiation.

10. The system of claim 1, wherein the fiber optic probe is configured as an optical fiber arrangement selected from the set of at least one of the following: radial, linear, matrix, 19-fiber to y-bundle.

11. The system of claim 1 further comprising a dichroic filter configured to separate a wavelength shifted beam of the beam of probe radiation onto a first optical path and the beam of probe radiation at an original wavelength onto a second optical path.

12. The system of claim 11 further comprising a fluorescence detector on the first optical path.

13. The system of claim 11 further comprising a Raman spectrometer on the first optical path.

14. The system of claim 13 wherein the Raman spectrometer is configured to analyze the wavelength shifted beam of probe radiation to produce a signal indicative of a Raman spectrum of a region of the sample illuminated by the beam of probe radiation.

15. The system of claim 1 further comprising a Raman spectrometer configured to analyze a wavelength shifted beam of the probe radiation to produce a signal indicative of a Raman spectrum of a region of the sample illuminated by the beam of probe radiation.

16. The system of claim 15, wherein the sample is one of a biological tissue or a biological cell, and wherein at least one of the signal indicative of infrared absorption and the signal indicative of the Raman spectrum is used to classify the one of the biological tissue or the biological cell.

17. The system of claim 1, wherein at least one of the infrared source and the probe source is a laser.

18. The system of claim 1, wherein at least one of the infrared source and the probe source is a broadband source.

19. The system of claim 1, wherein at least one of the infrared source and the probe source is tunable.

20. The system of claim 1, wherein the fiber optic probe comprises a bifurcated cable.

21. The system of claim 1, wherein the fiber optic probe is configured for handheld applications.

22. The system of claim 1, wherein the fiber optic probe further comprises an end piece.

23. The system of claim 22, wherein the end piece comprises at least one dichroic optic.

24. The system of claim 23, wherein the at least one dichroic optic combines the beam of infrared radiation and the beam of probe radiation onto a common path to the sample.

25. The system of claim 22 further comprising a port for optical viewing of the sample.

26. The system of claim 1, wherein the system is integrated into an endoscope.

27. The system of claim 1, where the sample is one of a biological tissue or a biological cell.

28. The system of claim 15, wherein at least one of the signal indicative of infrared absorption and the signal indicative of the Raman spectrum is used to identify at least one chemical species in the sample.

29. The system of claim 1, wherein the distal end of the fiber probe is inserted into a reaction chamber, and wherein the system is used to monitor reaction products in the reaction chamber.

30. The system of 29, wherein the system further comprises a Raman spectrometer.

31. The system of claim 1, wherein the distal end of the fiber probe has a diameter of less than 2 mm.

32. The system of claim 1, wherein the distal end of the fiber probe has a diameter of less than 1 mm.

33. The system of claim 1, wherein the distal end of the fiber probe has a diameter of less than 0.5 mm.

34. The system of claim 1 further comprising a plurality of focusing optics at the distal end of the fiber probe configured to collimate at least one of the beam of infrared radiation and the beam of probe radiation; and at least one focusing optic configured to focus the beam of infrared and the beam of probe radiation onto the sample.

35. An apparatus for fiber probe-based chemical analysis of a sample, the apparatus comprising:
a fiber optic bundle comprising a plurality of optical fibers, each of the plurality of optical fibers comprising a fiber optic distal end and a fiber optic proximal end, wherein the fiber optic bundle is bifurcated at the proximal end and wherein the plurality of optical fibers are each made of materials that are capable of transmitting light in both high water and low water environments, a source of pump radiation configured to illuminate the sample with a beam of pump radiation;
a source of probe radiation configured to illuminate the sample with a beam of probe radiation;
a beam splitter configured to divide the beam of probe radiation onto at least two paths;
a beam combiner configured to create an interference of the probe radiation reflected from the sample;
a detector configured to detect the interference of probe radiation and use the interference of probe radiation in producing a signal indicative of infrared absorption of the sample, wherein the signal indicative of the infrared absorption of the sample comprises an infrared absorption spectrum.

36. The apparatus of claim 35, further comprising a rugged casing to enclose the source of pump radiation, the source of probe radiation, the beam splitter, the beam combiner, and the detector.

37. A method of operating a system for fiber optic bundle-based spectroscopic analysis of a sample, the method comprising the steps of:
selecting a fiber optic bundle compatible with a sample matrix, a source of infrared radiation, and a source of probe radiation;
coupling a proximal end of the fiber optic bundle to a device containing a source of pump radiation and a source of probe radiation, such that a first subset of fibers of the fiber bundle receive light from the source of pump radiation and a second subset of fibers of the fiber bundle receive light from the source of probe radiation;
placing a distal end of the fiber optic bundle in proximity to the sample;
illuminating the sample with light from the source of pump radiation transmitted from the first subset of fibers to create an infrared illuminated spot on the sample;
illuminating the sample with light from the source of probe radiation transmitted from the second subset of fibers at the illuminated spot;
collecting probe radiation from the plurality of sample locations via the fiber optic bundle as collected probe radiation;
transmitting the collected probe radiation from the plurality of sample locations from the fiber optic distal end to the fiber optic proximal end of the fiber optic bundle;
detecting the collected probe radiation with at least one detector as detected probe radiation; and
analyzing the detected probe radiation to generate a signal indicative of infrared absorption of the plurality of locations on the sample, wherein the signal indicative of the infrared absorption comprises an infrared absorption spectrum.

* * * * *